(12) United States Patent
Smith et al.

(10) Patent No.: US 10,460,920 B1
(45) Date of Patent: Oct. 29, 2019

(54) FLEXIBLE ION CONDUIT

(71) Applicant: Battelle Memorial Institute, Richland, WA (US)

(72) Inventors: Richard D. Smith, Richland, WA (US); Sandilya V. B. Garimella, Richland, WA (US); Yehia M. Ibrahim, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 16/019,397

(22) Filed: Jun. 26, 2018

(51) Int. Cl.
*G01N 27/62* (2006.01)
*H01J 49/06* (2006.01)
*H01J 49/42* (2006.01)
*H01J 49/14* (2006.01)

(52) U.S. Cl.
CPC .......... *H01J 49/062* (2013.01); *G01N 27/622* (2013.01); *H01J 49/142* (2013.01)

(58) Field of Classification Search
CPC .......... H01J 49/062; H01J 49/42; H01J 49/00; H01J 49/0004; H01J 49/0013; H01J 49/0018; H01J 49/0022; H01J 49/004; H01J 49/26; H01J 49/0009; H01J 49/0027; H01J 49/0031; H01J 49/0036; H01J 49/426; G01N 27/622; G01N 30/72; G01N 27/624; G01N 33/6848
USPC .................................................. 250/281, 282
See application file for complete search history.

(56) References Cited

U.S. PATENT DOCUMENTS

| | | |
|---|---|---|
| 5,572,035 A | 11/1996 | Franzen |
| 6,107,328 A | 8/2000 | Parsons |
| 6,369,383 B1 | 4/2002 | Cornish et al. |
| 6,960,760 B2 | 11/2005 | Bateman et al. |
| 7,365,317 B2 | 4/2008 | Whitehouse et al. |
| 7,391,021 B2 | 7/2008 | Stoermer et al. |
| 7,786,435 B2 | 8/2010 | Whitehouse et al. |
| 7,838,826 B1 | 11/2010 | Park |
| 7,888,635 B2 | 2/2011 | Belov et al. |
| 8,049,169 B2 | 11/2011 | Satake et al. |
| 8,222,597 B2 | 7/2012 | Kim et al. |
| 8,637,817 B1 | 1/2014 | Krutchinsky et al. |
| 8,835,839 B1 | 9/2014 | Anderson et al. |

(Continued)

FOREIGN PATENT DOCUMENTS

| | | |
|---|---|---|
| EP | 1 566 828 A2 | 8/2005 |
| EP | 1 825 495 B1 | 11/2011 |

(Continued)

OTHER PUBLICATIONS

Ibrahim et al., "New frontiers for mass spectrometry based upon structures for lossless ion manipulations," The Analyst, 142(7):1010-1021 (Mar. 3, 2017).

(Continued)

*Primary Examiner* — Nicole M Ippolito
*Assistant Examiner* — Hanway Chang
(74) *Attorney, Agent, or Firm* — Klarquist Sparkman, LLP

(57) ABSTRACT

An apparatus includes a flexible ion conduit extending between an input end situated to receive ions and an output end to define an ion passageway having an axis, the flexible ion conduit including an inner conduit portion having an inner surface facing the interior ion passageway and having a plurality of RF electrodes adjacently situated to receive RF voltages that are out of phase with respect to each other to direct the received ions away from the inner surface and into the ion passageway.

37 Claims, 19 Drawing Sheets

(56) References Cited

U.S. PATENT DOCUMENTS

| | | | |
|---|---|---|---|
| 8,969,800 | B1 | 3/2015 | Tolmachev et al. |
| 9,324,548 | B1 | 4/2016 | Benter et al. |
| 2004/0026611 | A1 | 2/2004 | Bateman et al. |
| 2007/0138384 | A1 | 6/2007 | Keiser |
| 2009/0173880 | A1 | 7/2009 | Bateman et al. |
| 2009/0206250 | A1 | 8/2009 | Wollnik |
| 2011/0024618 | A1 | 2/2011 | Brown et al. |
| 2011/0049357 | A1 | 3/2011 | Giles |
| 2011/0192969 | A1 | 8/2011 | Verentchikov |
| 2012/0261570 | A1 | 10/2012 | Shvartsburg et al. |
| 2013/0175440 | A1 | 7/2013 | Perelman et al. |
| 2015/0076343 | A1 | 3/2015 | Tomachev et al. |
| 2016/0225598 | A1 | 8/2016 | Ristroph |
| 2016/0322209 | A1 | 11/2016 | Wouters et al. |
| 2017/0076931 | A1 | 3/2017 | Ibrahim et al. |

FOREIGN PATENT DOCUMENTS

| | | |
|---|---|---|
| EP | 3038134 | 6/2016 |
| EP | 3252460 | 12/2017 |
| GB | 2499587 | 8/2013 |
| WO | WO 2016/034125 | 3/2016 |
| WO | WO 2018/048494 | 3/2018 |

OTHER PUBLICATIONS

International Search Report and Written Opinion for related International Application No. PCT/US2018/065380, dated Mar. 29, 2019, 18 pages.

Garimella et al., "Simulation of Electric Potentials and Ion Motion in Planar Electrode Structures for Lossless Ion Manipulations (SLIM)," J. Am. Soc. Mass Spectrom. 25(11):1890-1896 (Nov. 2014).

Giles et al., "A method for direct measurement of ion mobilities using a travelling wave ion guide," International Journal of Mass Spectrometry, 298(1):10-16 (Dec. 2010).

Giles et al., "Applications of a travelling wave-based radio-frequency-only stacked ring ion guide," Rapid Commun. Mass Spectrom., 18(20):2401-2414 (Oct. 30, 2004).

Giles et al., "Enhancements in travelling wave ion mobility resolution," Rapid Commun. Mass Spectrom., 25(11):1559-1566 (Jun. 15, 2011).

Glaskin et al., "Ion Trapping for Ion Mobility Spectrometry Measurements in a Cyclical Drift Tube," Anal. Chem., 85(15):7003-7008 (Jul. 2013).

Hamid et al., "Characterization of Traveling Wave Ion Mobility Separations in Structures for Lossless Ion Manipulations," Anal. Chem., 87:11301-11308 (Oct. 28, 2015).

Ibrahim et al., "Development of a new ion mobility (quadrupole) time-of-flight mass spectrometer," International Journal of Mass Spectrometry, 377:655-662 (Feb. 1, 2015).

International Search Report and Written Opinion for related International Application No. PCT/US14/11291, dated Jun. 6, 2014.

International Search Report and Written Opinion for related International Application No. PCT/US2017/039770, dated Dec. 15, 2017.

Merenbloom et al., "Effects of Select Anions from the Hofmeister Series on the Gas-Phase Conformations of Protein Ions Measured with Traveling-Wave Ion Mobility Spectrometry/Mass Spectrometry," J. Am. Soc. Mass Spectrom. 22:1978-1990 (Nov. 22, 2011).

PCT Recordation of Search History for International Application No. PCT/US14/11291, International Filing Date Jan. 13, 2014, Date during which the search was conducted May 15, 2014, Date of Completion of Recordation of Search History Form May 22, 2014.

Pringle et al., "An investigation of the mobility separation of some peptide and protein ions using a new hybrid quadrupole/travelling wave IMS/oa-ToF instrument," International Journal of Mass Spectrometry, 261(1):1-12 (Mar. 1, 2007).

Shvartsburg et al., "Fundamentals of Traveling Wave Ion Mobility Spectrometry," Anal. Chem., 80(24):9689-9699 (Dec. 15, 2008).

Smith et al., "Deciphering drift time measurements from travelling wave ion mobility spectrometry-mass spectrometry studies," European Journal of Mass Spectrometry, 15(2):113-130 (Jan. 2009).

Sobott et al., "A Tandem Mass Spectrometer for Improved Transmission and Analysis of Large Macromolecular Assemblies," Anal. Chem., 74(6):1402-1407 (Apr. 2002).

Tolmachev et al., "Characterization of Ion Dynamics in Structures for Lossless Ion Manipulations," Anal. Chem., 86(18):9162-9168 (Sep. 16, 2014).

Webb et al., "Experimental Evaluation and Optimization of Structures for Lossless Ion Manipulations for Ion Mobility Spectrometry with Time-of-Flight Mass Spectometry," Anal. Chem., 86(18):9169-9176 (Sep. 5, 2014).

Webb et al., "Mobility-Resolved Ion Selection in Uniform Drift Field Ion Mobility Spectrometry/Mass Spectrometry: Dynamic Switching in Structures for Lossless Ion Manipulations," Anal. Chem., 86(19):9632-9637 (Oct. 7, 2014).

Zhang et al., "Ion Trapping, Storage, and Ejection in Structures for Lossless Ion Manipulations," Anal. Chem., 87(12):6010-6016 (May 2015).

Zhong et al., "Characterizing the resolution and accuracy of a second-generation traveling-wave ion mobility separator for biomolecular ions," The Royal Society of Chemistry, 136(17):3534-3541 (Mar. 2011).

International Search Report and Written Opinion for related International Application No. PCT/US2019/039302, dated Sep. 20, 2019, 11 pages.

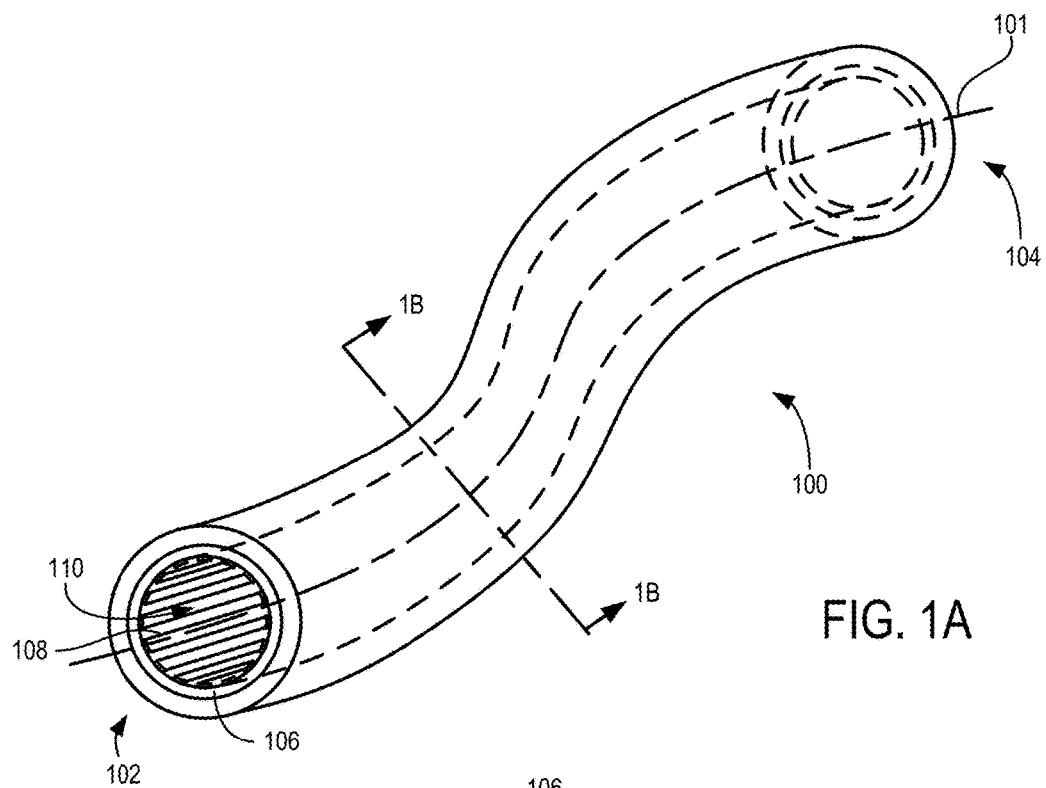
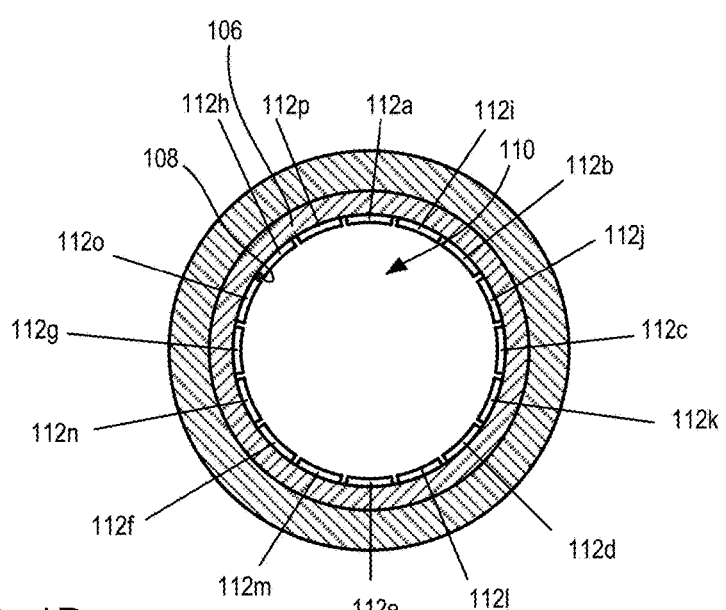

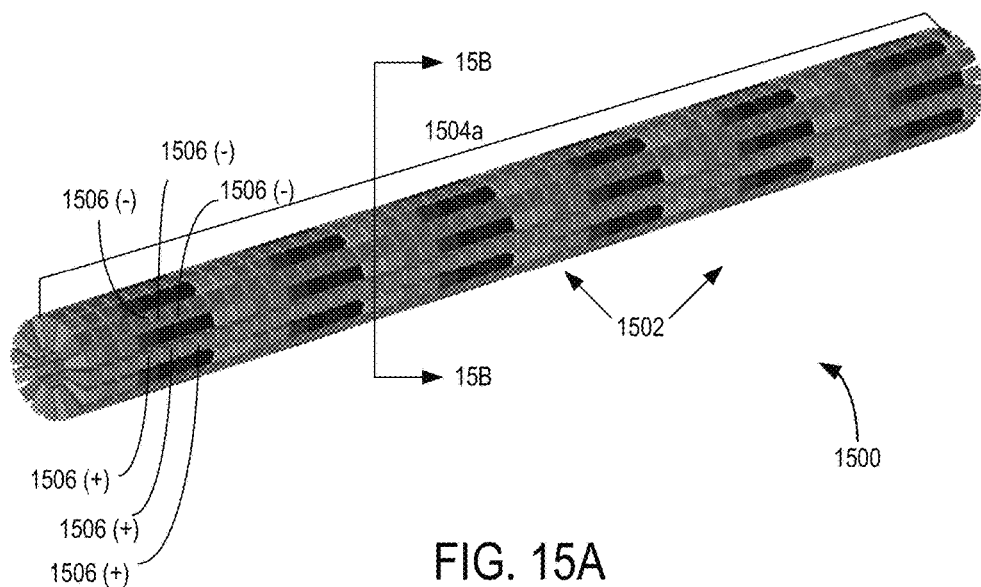
FIG. 15A
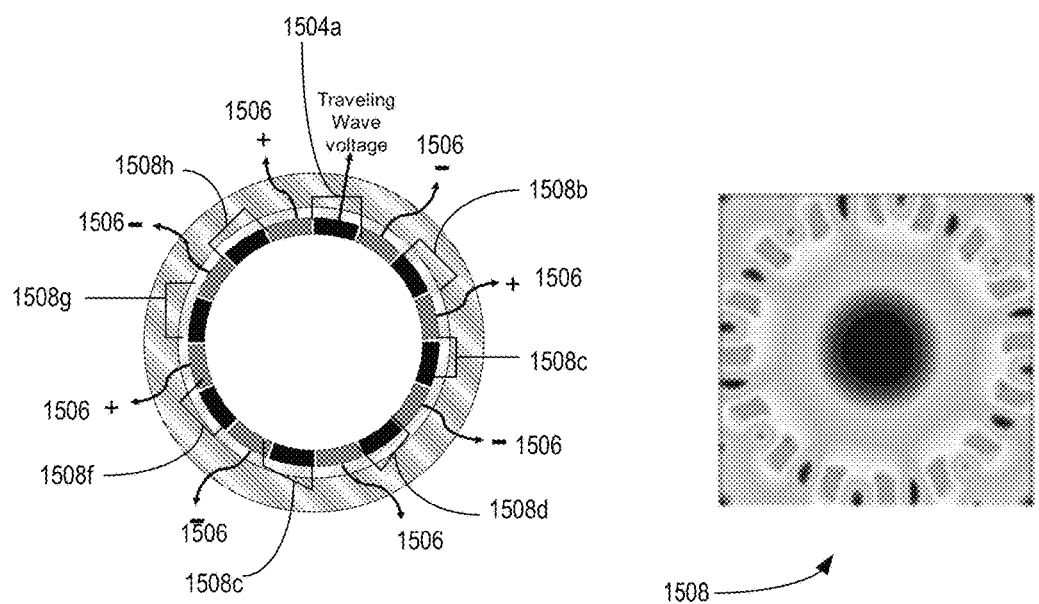
FIG. 15B
FIG. 15C

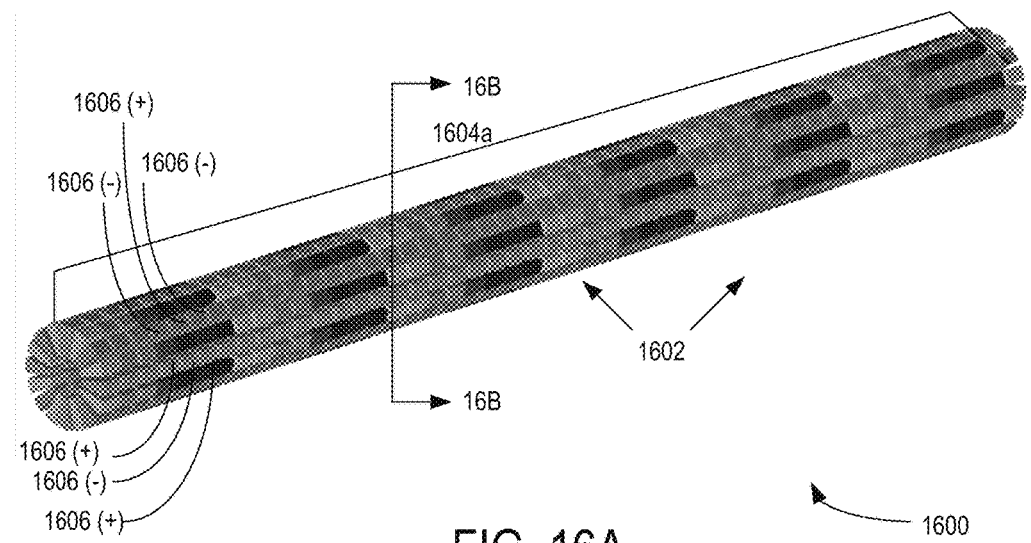
FIG. 16A
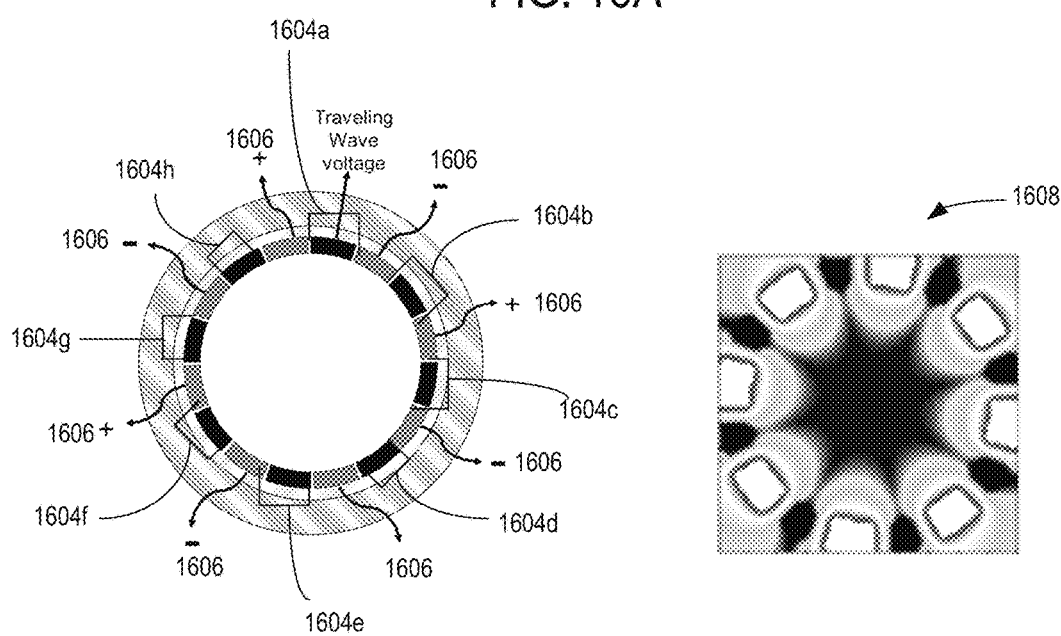 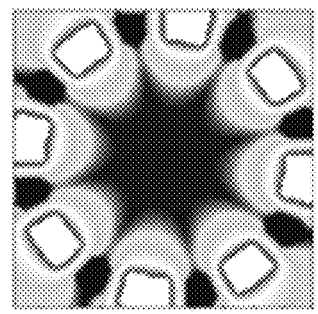
FIG. 16B FIG. 16C

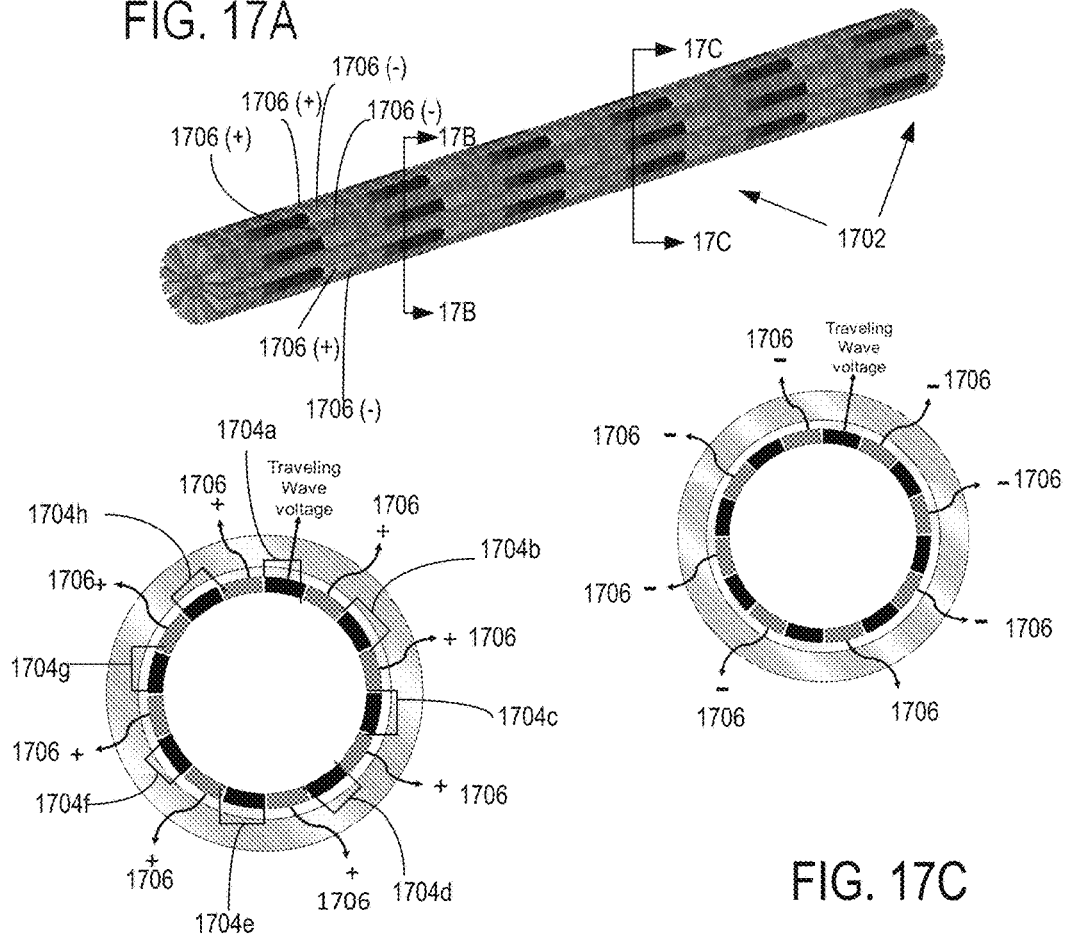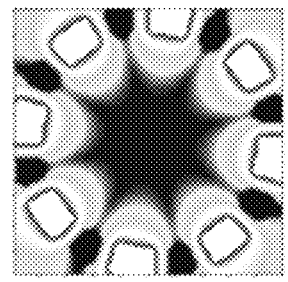

under DE-AC05-76RL01830 awarded by the United States
FLEXIBLE ION CONDUIT

ACKNOWLEDGMENT OF GOVERNMENT SUPPORT

This invention was made with government support under DE-AC05-76RL01830 awarded by the United States Department of Energy and under Grant No. GM103493 awarded by the National Institutes of Health. The government has certain rights in the invention.

FIELD

The field is ion manipulation and transfer within ion conduits.

BACKGROUND

Various applications require transport and manipulation of ions to achieve different goals, such as using mass spectrometry, particle detection, etc. However, lossless or low loss ion transport and/or separation is often desired or required, and remains difficult to achieve over any significant distances, such as between a source of ions and an ion analyzer. Furthermore, to provide ion mobility separations, devices often must be specifically designed with particular structures to generate the required electric fields, and often be optimized for particular applications. Therefore, a need remains for improvements in the field of ion transport and manipulation.

SUMMARY

According to an aspect of the disclosed technology, apparatus include a flexible ion conduit extending between an input end situated to receive ions and an output end to deliver ions and defining an ion passageway, the flexible ion conduit including an inner conduit portion having an inner surface facing the interior ion passageway and having a plurality of RF electrodes situated to receive RF voltages wherein each RF voltage is out of phase with respect to the RF voltage applied to a nearest RF electrode of the RF electrodes to direct the received ions away from the inner surface of the ion passageway. In some examples, at least four of the RF electrodes extend along the inner surface for an entire length of the flexible ion conduit between the input end and the output end. In further examples, at least four of the RF electrodes extend along the inner surface for at least a portion of the length of the flexible ion conduit. In particular examples, the plurality of RF electrodes is an even numbered quantity. In some examples, the portion is at least 80% of the length.

In some embodiments, the inner conduit portion is cylindrical or deviates from a cylindrical by being elliptically cylindrical for some or all of a length of the flexible ion conduit. In further embodiments, the inner conduit portion includes a plurality of electrodes positioned between the RF electrodes and that is situated to receive AC or DC voltages and that forms an electrode set that extends along the inner surface for at least a portion of the length of the flexible ion conduit. In still further embodiments, the inner conduit portion includes a plurality of traveling wave electrodes positioned between the RF electrodes and forming a set that extends along the inner surface for at least a portion of the length of the flexible ion conduit and that is situated to receive traveling wave voltages to form a traveling wave. In some examples, the RF electrodes are laterally separated from each other by non-conductive gaps of 30 µm or smaller but larger than a gap that causes an electrical breakdown between the RF electrodes. In additional examples, the flexible ion conduit is situated to move ions along the ion passageway between the input end and the output end over a range of pressures based on a conduit length, cross-section, and gas flow. In some traveling wave electrode examples, the traveling wave voltages correspond to time-varying DC voltages or phase shifted AC voltages. In further traveling wave electrode examples, the set of traveling wave electrodes and the traveling wave voltages are configured to direct the received ions from the input end to the output end. In additional traveling wave electrode examples, the set of traveling wave electrodes and the traveling wave voltages are configured to receive and transmit ions of both positive and negative polarity simultaneously. In further traveling wave electrode examples, the set of traveling wave electrodes and the traveling wave voltages are configured to simultaneously receive, transmit, and separate ions of both positive and negative polarity based on their ion mobilities. According to still further traveling wave electrode examples, the set of traveling wave electrodes and the traveling wave voltages are configured to separate ions in the ion passageway based on ion mobility, m/z, and/or ion charge.

In selected examples, the output end is configured to couple to a low pressure ion inlet for the low pressure ion inlet to receive the ions from the ion passageway. In particular examples, the low pressure ion inlet is a mass analysis region of a mass spectrometer or an ion introduction component of the mass spectrometer ion inlet that is configured to deliver ions to the mass spectrometer. In some embodiments, the low pressure ion inlet is a structure for lossless ion manipulation (SLIM) ion inlet.

Some embodiments can further include a detector coupled to output end to detect one or more characteristics of the ions.

In some examples, the flexible ion conduit comprises a bendable sheath surrounding the inner conduit portion and that supports the inner conduit portion and a pressure differential between an external pressure outside of the flexible ion conduit and an internal pressure in the ion passageway interior. In particular embodiments, the external pressure is an ambient pressure.

In some examples, the RF electrodes are configured to losslessly direct the ions into the ion passageway away from the inner surface across a predetermined range of bend radii of the flexible ion conduit.

In representative examples, the inner conduit portion contains arrays of electrodes patterned on a flexible printed circuit substrate. In particular examples, the output end is tapered.

Some examples can further include an intersection coupling coupled to the output end and including a plurality of output ion paths for ions transported along the ion passageway. In selected examples, the intersection coupling is a T-shaped, Y-shaped, or cross-shaped intersection coupling.

According to another aspect of the disclosed technology, methods include printing an electrode pattern of RF electrodes on a flexible printed circuit board to form the inner conduit surface of a flexible ion conduit, and securing the inner conduit surface in relation to a flexible sheath to form the flexible ion conduit.

According to a further example, a method includes exposing an ion inlet of an ion receiving device, and coupling a flexible ion conduit to the ion inlet to provide an ion source for the ion receiving device. In some examples, the ion inlet is a low pressure inlet of the ion receiving device. In further examples, the exposing comprises removing an existing ion source mechanism coupled to the ion receiving device. Some methods, can further include adapting an input aperture of the low pressure inlet to an output aperture of the flexible ion conduit. In particular examples, the ion receiving device is at least one of a mass spectrometer, ion mobility analyzer, structure for lossless ion manipulation (SLIM), liquid or gas chromatograph, and ion mobility spectrometer. Some method examples can further include coupling the input end of the flexible ion conduit to an output of a structure for lossless ion manipulation, wherein the ion receiving device is a mass spectrometer. In still further examples, the ion receiving device is an intersection coupling providing a plurality of selectable ion paths.

Some methods can include moving or separating the ions along the ion passageway of a flexible ion conduit.

According to some embodiments, apparatus can include a flexible ion conduit, and a controller coupled to the flexible ion conduit and configured to control the RF voltages applied to the RF electrodes.

In still further embodiments, apparatus can include a flexible ion conduit with traveling wave electrodes, and a controller coupled to the flexible ion conduit and configured to control the traveling wave voltages applied to the set of traveling wave electrodes.

The foregoing and other objects, features, and advantages of the disclosed technology will become more apparent from the following detailed description, which proceeds with reference to the accompanying figures.

BRIEF DESCRIPTION OF THE DRAWINGS

FIG. 1A shows a perspective view of an example flexible ion conduit.

FIG. 1B shows a cross-section view of the example flexible ion conduit shown in FIG. 1A.

FIGS. 15A-15C show an example of a flexible ion conduit in a perspective view, in cross-section, and in cross-section during simulated operation.

FIGS. 16A-16C show another example of a flexible ion conduit in a perspective view, in cross-section, and in cross-section during simulated operation.

FIGS. 17A-17D show another example of a flexible ion conduit in a perspective view, in separate cross-sections, and in cross-section during simulated operation.

DETAILED DESCRIPTION

Figure 2A:
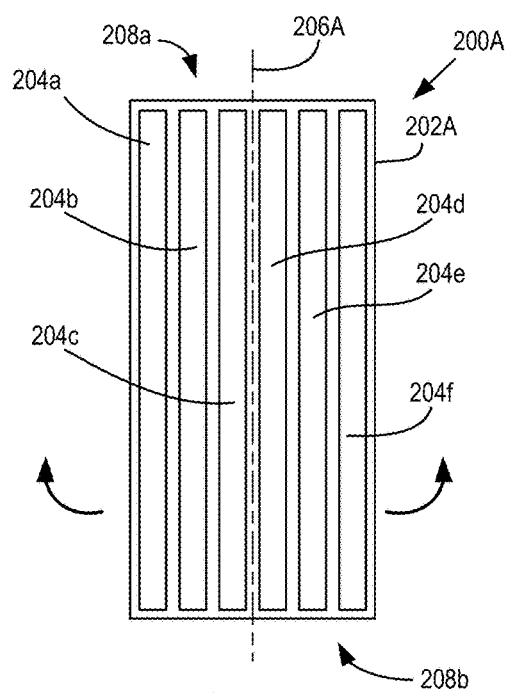
FIGS. 2A-2D show plan views of electrode arrangements that can be used in different flexible ion conduit examples.
Figure 2B:
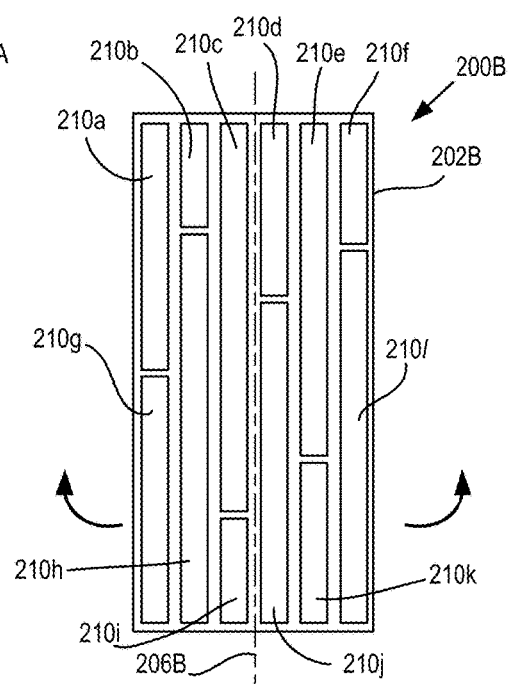
Figure 2C:
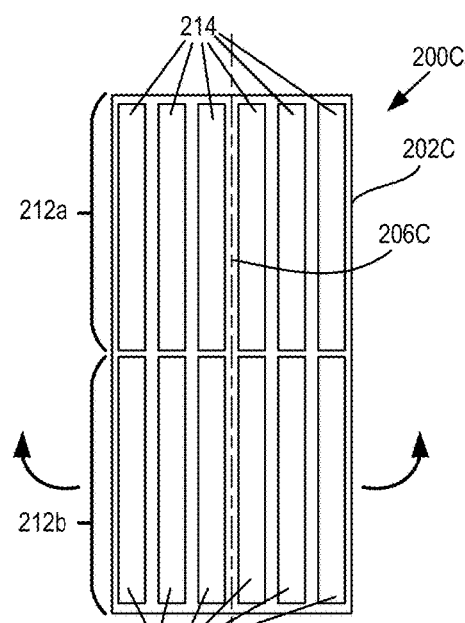
Figure 2D:
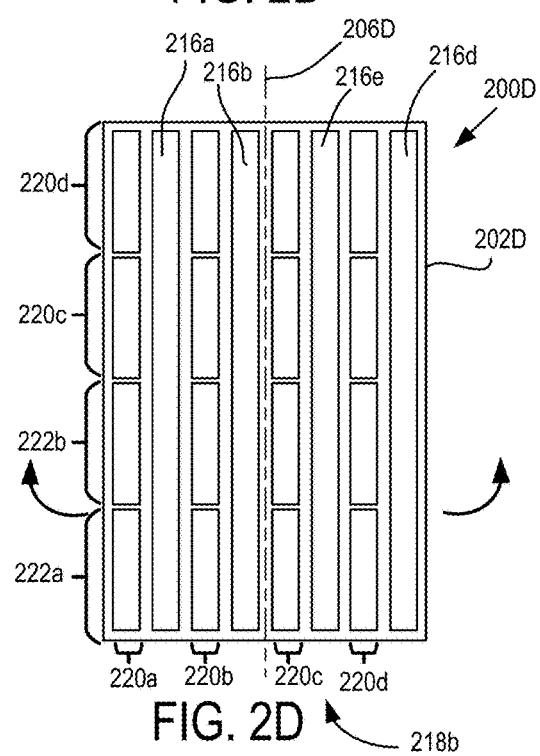
Figure 2E:
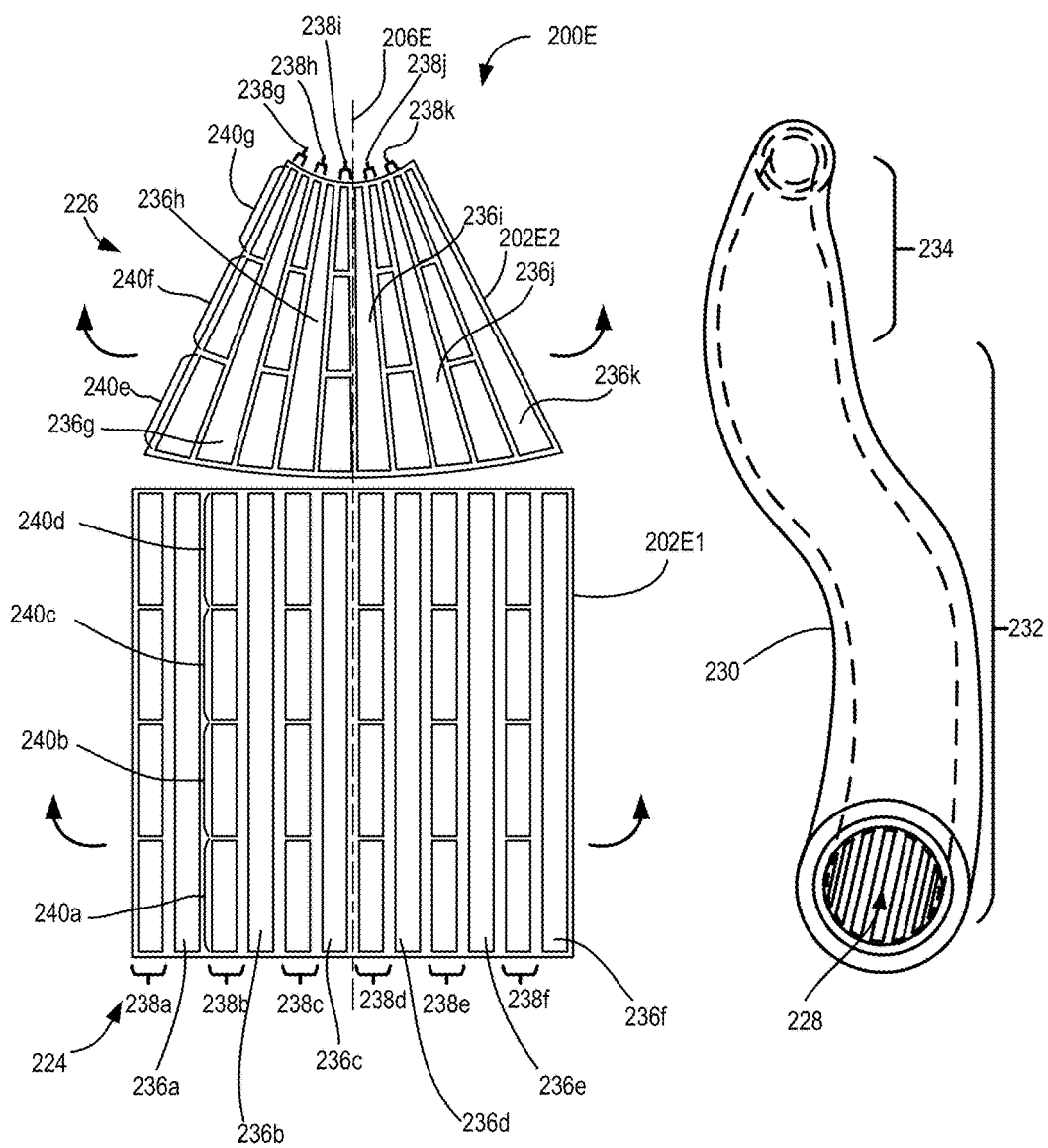
FIG. 2E shows a plan view of an electrode arrangement and a related flexible ion conduit using the electrode arrangement.
Figure 2F:
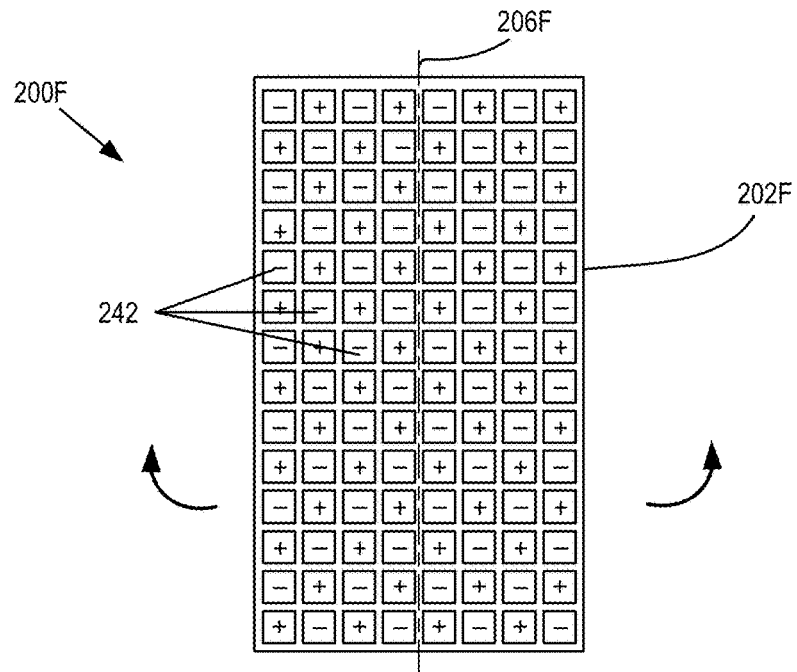
FIGS. 2F-2I show plan views of other electrode arrangements that can be used in different flexible ion conduit examples.
Figure 2G:
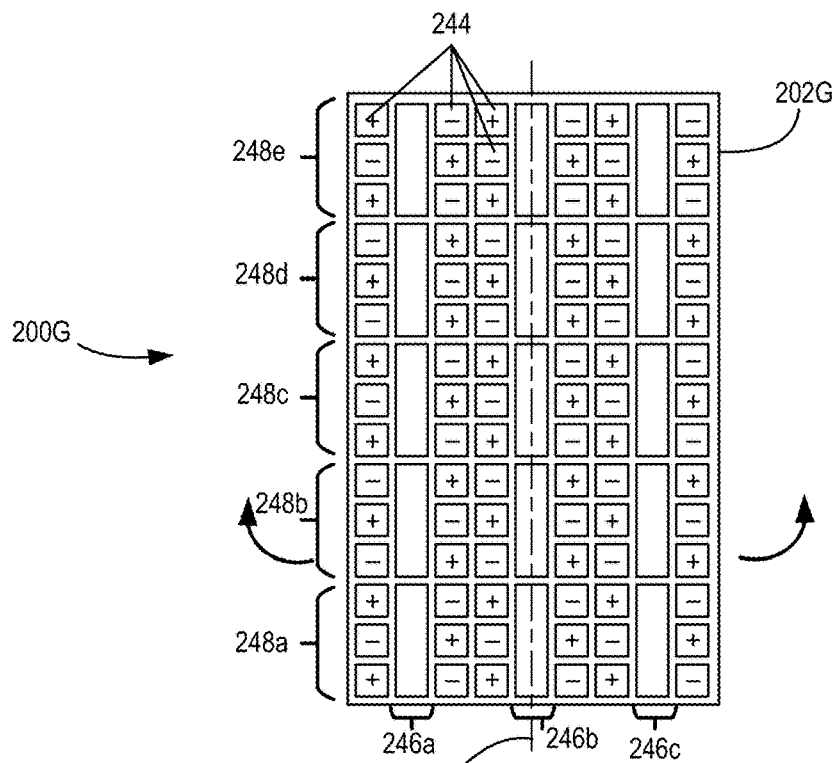
Figure 2H:
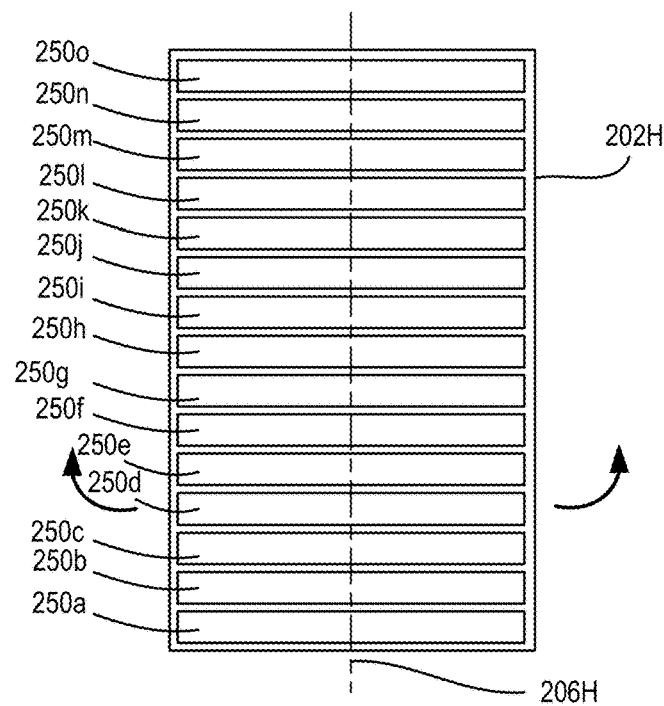
Figure 2I:
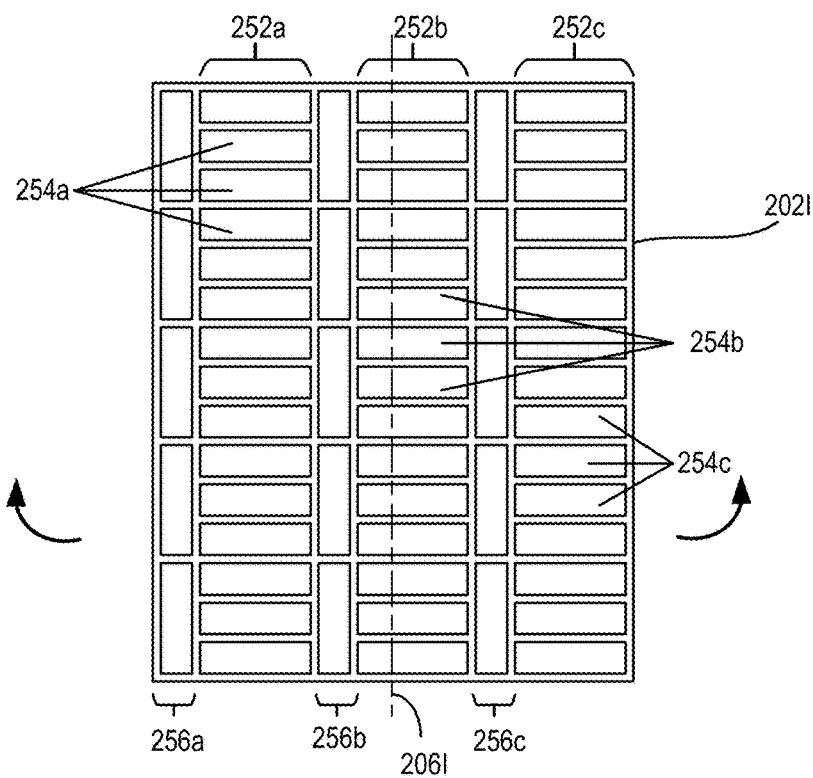

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art. In some examples, values, procedures, or apparatus' are referred to as "lowest", "best", "minimum," or the like. It will be appreciated that such descriptions are intended to indicate that a selection among many used functional alternatives can be made, and such selections need not be better, smaller, or otherwise preferable to other selections.

Some examples are described in relation to one more longitudinal and lateral directions generalized to correspond to ion movement or confinement respectively. Directions typically apply to ion movement, trapping, and confinement and are provided by electric fields produced by electrodes that are arranged on the inner surface of the flexible conduit to define one or more flexibly defined volumes of various shapes, sizes, and configurations. Actual ion movement paths vary and can depend on the various characteristics of the electrode arrangements and electric fields produced by the corresponding electrodes and the positional, polarity, kinetic, or other characteristics of the ions received in a confinement volume. Directions referred to herein are generalized and actual specific particle movements typically correspond to electric fields produced and the electrical mobilities of the ions propagating in relation to the electric fields, as well as gas flow movements in some embodiments.

The disclosed technology is directed to devices, apparatus, and methods of manipulating, separating, or transporting ions, including the use of electric fields to create field-defined pathways, traps, conduits, and switches to manipulate ions with minimal or no losses in gases over a wide range of pressures.

In representative embodiments herein, which can be referred to as Flexible Lossless Ion Path (FLIP) devices, devices are constructed from flexible non-conductive or low conductivity materials capable of being configured in shapes such as tubes with enclosed volumes and on which conductive electrodes with electric potentials provided to the electrodes that are positioned on the internal surface to enable ion movement along the path defined by the device. The conduit or path defined by the device (e.g., the ion path) can be fabricated from a flexible substrate, and can be particularly suited where flexibility is desired in use as opposed to a rigid non-linear path (e.g., a conduit that is not flexible but having a curve, bend, or more complex shape) and patterned with electrodes to the extent that the substrate can be flexibly curved or bent in either case and enabling the enclosed confinement ion path. Flexible substrate examples include deposited, printed, or otherwise positioned electrodes to which electric potentials are applied that provide for ion confinement over a flexible ion paths, including flexible non-linear ion paths. The electrodes are powered by an external power supply or supplies (e.g., voltage sources), and are positioned on the interior surface of the flexible substrate. The electrodes can be provided with various combinations of RF and DC (static or dynamic) potentials applied that are used to confine or move ions along the flexible or non-linear path while also confining the ions within a cross section (i.e. some finite distance from the inner wall) of the volume created by the FLIP device to minimize or eliminate ion loss. The combination of RF and DC electrodes can be any arrangement whereby ions can remain within the cross-section of the FLIP device and the path of the ions within the device is linear, non-linear or flexible due to the flexibility of the substrate. Embodiments can also include more complex physical shapes that enclose FLIP regions used for switching ions between two or more alternative ion paths, such as 'tee' shaped or 'cross' shaped where each arm or conduit segment has an enclosed path except for a region of intersection.

Some example arrangements/embodiments that can be used with FLIP devices wherein the ions remain confined inside and move along a linear, non-linear, or flexible path are described below. This is in no way restrictive and includes any number of ways by which a flexible substrate is patterned or printed with electrodes on it that assist or provide to confine and/or move ions along the defined paths. Other arrangements/embodiments involve the use of fixed non-linear and complex paths that utilize a rigid material fabricated to define a specific non-linear path for ion transport; such arrangement correspond to fixed path arrangements for which a complex path is desired, but conduit flexibility is not needed, and as such the flexibles substrate can be replace by a rigid substrate.

In some embodiments, complex sequences of ion separations, transfers, path switching, and trapping can occur in the volume defined by electrode arrays printed on flexible surfaces using photolithography, such as used for flexible printed circuit boards. In some examples, ion confining fields are provided by biased or unbiased radio frequency (RF) electric fields. RE electric fields are typically applied so that RF fields generated by adjacent RF electrodes are out of phase, typically by approximately 180°, to form a 'pseudo-potential' or an 'effective potential' that inhibits the ions in a predetermined adz range from approaching the electrodes and surfaces so as to provide ion confinement and inhibit ion losses. In other examples, the opposite phases of RF are interspersed with other electrodes which are either grounded, applied with a constant DC bias, or a dynamic potential, such as needed to create a traveling electric wave.

In some instances, ions of opposite polarity are moved, trapped, or manipulated using RF electric fields or RF and traveling wave electric fields. Confinement can be provided over a range of pressures (e.g., less than approximately 0.01 torr to approximately 1000 torr), and over a useful, broad, and adjustable mass to charge (m/z) range or ion mobility depending upon the electric potentials applied. Pressure ranges can be provided based on increasing length and reduced cross-section or conduit aperture such that a pressure drop can occur that results from a gas flow through the conduit. In some examples ions are manipulated for analysis through mass spectrometry or with a mass spectrometer coupled via FLIP conduits, and where pressures of less than approximately 0.1 torr to approximately 50 torr in the FLIP to manipulate ions over a useful m/z range, e.g., m/z 20 to greater than approximately 5,000. In some examples, ion confinement volumes in the FLIP includes specific gases or other gas-phase reactants. Ions can have various ion mobilities. Herein, ion mobility is generally understood as corresponding to the ratio of ion drift velocity (through a gas) to electric field strength, and can be dependent upon ion mass, charge, size, or collision cross-section, and the characteristics of the gas medium through the ions move, including pressure, temperature, and composition.

Arrangements of electrodes receive corresponding potentials that allow creation or definition of ion traps and/or conduits in selected regions of the FLIP so that lossless or substantially lossless storage and/or movement of ions of the same or different polarities can be achieved. The electric potentials that can enable this include any combination of RE traveling waves with or without the concurrent application of static or superimposed DC or TW potentials. For example, lossless manipulation can include losses of less than 0.1%, 1%, or 5% of ions injected into a corresponding ion confinement volume.

Traveling waves are broadly useful for moving ions in FLIP, and can replace or augment motion due to gas flows, and are typically created by dynamically applying DC potentials or phase-shifted AC voltages to a plurality of electrodes arranged in one or more sequences. Traveling wave electrode sets can be formed by one or more sequences of electrodes arranged in a series and for which the electric potentials applied are changed in a time-dependent and repeating manner. As the potentials are varied between the array of electrodes, a traveling wave can be formed with a speed based on the time dependent variation of the DC potentials. Varying traveling wave characteristics, typically speed and amplitude, can affect and manipulate various movements of ions having different ion mobilities, including producing ion confinement, lossless transport, and ion separation. In some examples, in conjunction with traveling waves, ions can be losslessly confined in an ion confinement volume for greatly extended durations, such as multiple hours. One such characteristic is the traveling wave speed, with ions that have higher mobility moving or surfing with the traveling wave and ions that have lower mobility rolling over and lagging behind the traveling wave to provide a mobility dependent ion separation. Another such characteristic is traveling wave amplitude, which can transport ions with lower ion mobilities with a corresponding increase in traveling wave amplitude. Traveling wave amplitudes are typically selected based on ion mobility characteristics and the desired ion manipulation to be in the range of greater than 0 V up to 30 V, 50 V, 80 V, 100 V, or greater. Traveling wave speeds are typically higher at low pressures and lower at high pressures, and selected based on ion mobility characteristics, electric fields, and the desired ion manipulation to be in the range of less than 5 m/s, 20 m/s 50 m/s, 100 m/s, 200 m/s, or 500 m/s or greater. Traveling wave speeds will be lower or higher depending primarily on the mobility of the ions, electric fields, the specific details of electrode arrangements being used and the gas pressure in a specific FLIP embodiment. Similarly, traveling wave amplitudes at higher pressure are typically greater for ions of a specific mobility and wave speed, and often to achieve a specific ion mobility separation, an increased TW amplitude can be used to compensate for an increased TW speed.

In some embodiments, ion movement or separations can be enhanced or assisted with a gas flow. In some of these embodiments the direction of the gas flow is opposite in direction to that of the traveling wave, such that an ion having a specific mobility, or a limited range of mobilities, can be trapped in one location while ions of higher or lower mobility move forward and backward respectively.

FIGS. 1A-1B is an example of a flexible ion conduit 100 that extends between an input end 102 and an output end 104 and having an ion propagation axis 101. The flexible ion conduit 100 is configured to be flexible, bendable, or have a complex non-linear path, so that the input end 102 and the output end 104 can be positioned separately and so that the ion propagation axis 101 can form different paths. In some examples, the flexible ion conduit 100 does not have a predefined shape and/or linear path, and in further examples the flexible ion conduit 100 can have a predefined shape but is sufficiently bendable or flexible to have the shape change between or during use. In typical examples, the separately positionable input end 102 and output end 104 can be removably coupled to different devices, such as ion sources, mass spectrometers, ion manipulation devices, other flexible ion conduits, etc., with one or more conduit adapters, hose fittings, couplers, vacuum/gas quick connect/disconnects, etc. In representative examples, the flexible ion conduit 100 includes an inner conduit portion 106 with an inner surface 108 facing an interior volume of the flexible ion conduit 100 so as to define an ion passageway 110 that extends between the input end 102 and the output end 104. The inner conduit portion 106 can be made of, or include, a flexible printed circuit substrate having a plurality of adjacently patterned or printed radio frequency (RF) electrodes 112a-112p. In representative examples, the RF electrodes 112a-112p extend along the length of the ion passageway 110 for at least a portion of the length flexible ion conduit 100. The RF electrodes 112a-112p are patterned or printed on the inner surface 108 in a predetermined configuration, such as parallel and extending a common length (though other configurations are possible), and are situated to receive an RF voltage bias. In typical examples, the voltages of a first set of the alternate RF electrodes 112a-112h are modulated in phase with each other and a second set of the alternate RF electrodes 112i-112p are also modulated in phase with each other, but the second set is out of phase from the first set (e.g., by 180°). During operation, the biased RF electrodes 112a-112p provide electric fields in the ion passageway 110 that direct ions 114 in the ion passageway 110 away from the conduit surfaces and reduce loss of the ions 114, e.g., due to impact with the inner surface 108 or other parts of the flexible ion conduit 100. The RF electrodes can have various dimensions, including lengths that extend an entire or substantial portion of the length of the flexible ion conduit, which can be from centimeters to many meters in length. Width dimensions can scale with flexible ion conduit diameter or effective diameter. Suitable widths can include 1 cm, 0.5 cm, 0.1 cm, or 0.01 cm, by way of example. Suitable diameters or effective diameters (if not circular) for the ion passageway 110 can include 0.1 cm, 1 cm, 2 cm, 5 cm, 10 cm, etc. Suitable thicknesses of the patterned electrodes can include 0.0001 mm, 0.001 mm, 0.01 mm, 0.1 mm, 0.5 mm, 1 mm, etc.

An outer flexible sheath 116 can surround the inner conduit portion 106 and can provide structural support or additional structural support for the inner conduit portion 106 on which electrodes are patterned. During use, some embodiments of the flexible ion conduit 100 can experience and support a pressure differential between a higher pressure $P_{OUT}$ outside of the flexible ion conduit 100 (e.g., outside the outer flexible sheath 116), such as ambient or atmospheric, and a lower pressure $P_{IN}$ in the ion passageway 110, such as $0.9 \cdot P_{OUT}$, $0.5 \cdot P_{OUT}$, $0.1 \cdot P_{OUT}$, $0.01 \cdot P_{OUT}$, or $0.001 \cdot P_{OUT}$. The inner conduit portion 106 can be secured to the outer flexible sheath 116 with adhesive, fasteners, or another suitable attachment, and one or more other layers, sheaths, tubes, etc., can also be disposed between the outer flexible sheath 116 and inner conduit portion 106, such as one or more electrical insulating layers and/or electrical harness layers configured to route voltages to the plurality of RF electrodes 112a-112p (or other electrodes). Alternatively, electrical connections can be arranged on the outer side of inner conduit portion 106 of the flexible ion conduit 100, with electrical connections through conductive vias of the inner conduit portion 106, as used in printed circuit board technology. In example where a pressure difference between the ion passageway 110 and a local external environment is sufficiently small (e.g., both at ambient pressure), the flexible conduit 100 can be used without the outer flexible sheath 116. In some examples, the flexible sheath 116 is a rigid sheath member having a predetermined shape (e.g., cast, molded, etc.) or that is bent into a predetermined shape (e.g., bendable rigid tubing), including straight or complex non-linear shapes. The inner conduit portion 106 can correspond to the flexible ion conduit that can be inserted into the rigid sheath member.

The inner conduit portion 106 can be constructed from an initially flat flexible printed circuit substrate, such as one made of polymer, e.g. polyamide, etc., that can be rolled or bent to correspond to the interior dimensions of the outer flexible sheath 116, and in related examples, the inner conduit portion 106 can be secured in the cavity formed by the outer flexible sheath 116 when such an outer sheath may be used, based on flexural urging of the inner conduit portion 106 to return to the initially flat position. The initially flat flexible printed circuit substrate can also be rolled and have seams secured with tape, Velcro, one or more outer supports (e.g., an outer tube or cage), adhesive, etc. Printed circuit substrates can be fabricated to various thicknesses, with flexural rigidity typically increasing with increased thickness, with example thicknesses that can include 25 µm, 50 µm, 100 µm, 200 µm, 500 µm, or thicker. The inner conduit portion 106 can include one or more conductive traces or trace layers that allow voltages to be routed to the different RF electrodes 112a-112p from an outside voltage source (e.g., through a wiring harness and/or plug). In typical examples, the flexible sheath 116 is made of a suitably rigid, thick-walled, and flexible material, such as metal, plastic, or rubber vacuum tubing. In some examples, the rigidity of the flexible sheath 116 provides lateral flexure (e.g., perpendicular to an ion propagation direction) such that a cross-sectional shape of the ion passageway 110 can vary without substantially increasing loss of the ions 114 or affecting efficiency of ion transfer and/or separation. For example, bending of the flexible ion conduit 100 can cause a circular cross-section can become elliptical, opposite sides of a rectangular cross-section can bow in or out, etc. In some examples, the flexible sheath 116 can restrictively limit or include a layer that restrictively limits bending of the flexible ion conduit 100 to a predetermined amount, such as maximum bend radius associated with the ion propagation axis 101 or maximum deflection or ellipticity of a cross-section, that may be associated with an ion transport loss or reduced ion separation efficacy. In representative implementations, ion transport along the flexible ion conduit 100 can be accomplished losslessly or with low loss at various bendable positions of the flexible ion conduit 100. In some examples, the ion transport can be performed during bending or manipulation of the flexible ion conduit 100 into different positions.

Figure 13:
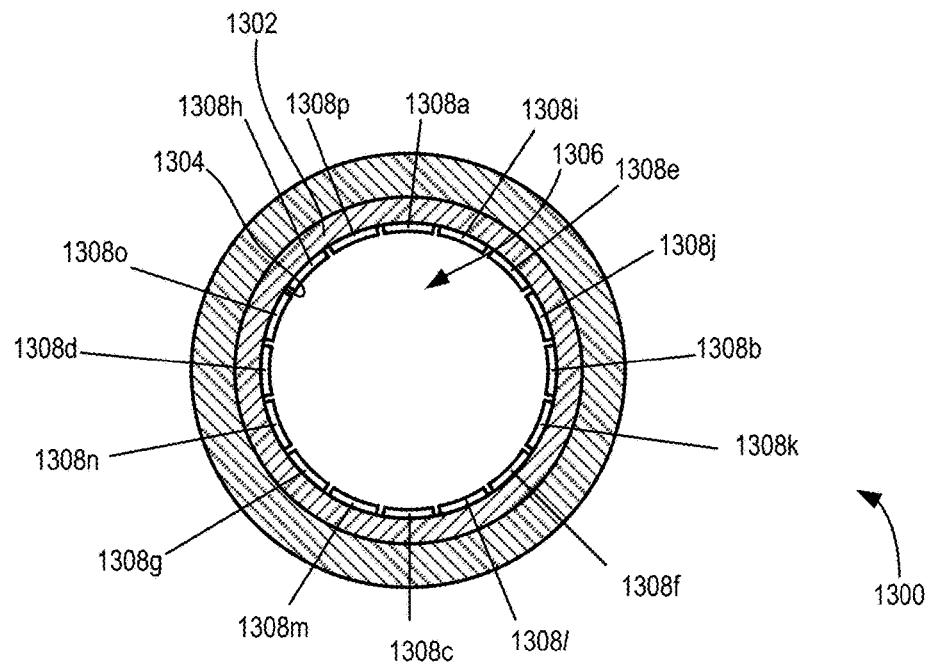
FIG. 13 show a cross-section view of an example flexible ion conduit.
Figure 14:
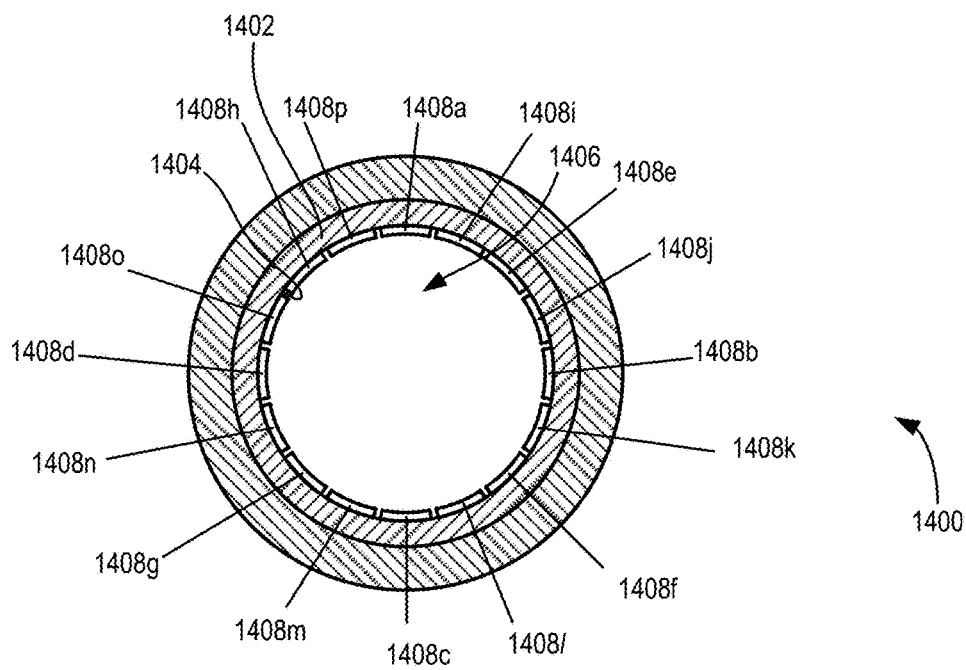
FIG. 14 show a cross-section view of another example flexible ion conduit.

FIG. 13 shows a cross-section of a flexible ion conduit 1300 which is similar in many respects to the flexible ion conduit 100 shown in FIG. 1. The flexible ion conduit 1300 includes an inner conduit portion 1302 with an inner surface 1304 defining an ion passageway 1306. A plurality of electrodes 1308a-1308p are defined on the inner surface 1304 and face the ion passageway 1306. The electrodes 1308a-1308h correspond to RF electrodes, with electrodes 1308a-1308d being in phase with each other and electrodes 1308e-1308h being in phase with each other but 180 degrees out of phase with respect to electrodes 1308a-1308d. Electrodes 1308i-1308p correspond to DC electrodes that receive a common ground voltage. FIG. 14 shows a cross-section of a flexible ion conduit 1400 which is similar to the flexible ion conduit 1300 in some respects. The flexible ion conduit 1400 includes an inner conduit portion 1402 with an inner surface 1404 defining an ion passageway 1406. A plurality of electrodes 1408a-1408p are defined on the inner surface 1404 and face the ion passageway 1406. The electrodes 1408a-1408h correspond to RF electrodes, with electrodes 1408a-1408d being in phase with each other and electrodes 1408e-1408h being in phase with each other but 180 degrees out of phase with respect to electrodes 1408a-1408d. However, in the flexible ion conduit 1400, the electrodes 1408i-1408p correspond to traveling wave DC electrodes. The electrodes 1408i-1408p receive a time-dependent DC electrode bias that forms a traveling wave to move or separate ions in the ion passageway 1406. In typical examples, the electrodes 1408a-1408i at the cross-sectional position receive a common time-dependent bias, and other traveling wave electrodes at different cross-sectional positions along the length of the flexible ion conduit 1400 receive a different common bias according to the time dependent characteristics of the traveling wave.

FIGS. 2A-2G are representative electrode arrangements 200A-200G formed on respective flexible substrates 202A-202F, 202G1-202G2 shown in flat configurations before folding (indicated by arrows) and/or conduit assembly to define tubular ion passageways. The electrode arrangement 200A includes a plurality of RF electrodes 204a-204f that extend along an axial direction, e.g., parallel to an ion propagation axis 206A, between opposite input/output ends 208a, 208b. As shown, the six RF electrodes 204a-204f have a lateral width and are laterally spaced apart from each other by a sufficient distance so that the RF electrodes 204a-204f do not contact or short when the flexible substrate 202A becomes folded into a nominal position in an unbent conduit or with normal bending during use. The RF electrodes 204a, 204c, 204e typically receive a first RF potential and the RF electrodes 204b, 204d, 204f receive a second RF potential (typically equal in amplitude) that is out of phase by 180 degrees. Representative RF frequencies include 0.1 MHz to 5 MHz. While the electrode arrangement 202A has six electrodes as shown, it will be appreciated that other examples can include different numbers of electrodes, with even quantities being typical, such as 8 electrodes, 10 electrodes, 12 electrodes, 14 electrodes, 16 electrodes, 18 electrodes, 20 electrodes, or greater numbers of RF electrodes. For convenience of illustration, the various electrode arrangements 200A-200G are generally depicted with an aspect ratio that is on the order of unity. While such examples are possible, it will be appreciated that certain examples can have substantial lengths with respect to diameter or effective diameter, such as lengths in the range of 10s of centimeters to meters and diameters in the range of centimeters, by way of example.

The electrode arrangement 200B includes a plurality of RF electrodes 210a-210l extending parallel to an ion propagation axis 206B. The RF electrodes 210a-210f extend and terminate and the RF electrodes 210g-210l begin and extend from the respective electrodes 210a-210f at predetermined or randomly staggered positions along the ion propagation axis 206B. In the electrode arrangement 200C, two groups 212a, 212b of adjacent RF electrodes 214 extend axially along an ion propagation axis 206C.

The electrode arrangement 200D includes a plurality of RF electrodes 216a-216d with adjacent electrodes having alternate polarities, such that RF electrodes 216a, 216c are in phase with each other and 180 degrees out of phase with RF electrodes 216b, 216d. The RF electrodes 216a-216d extend along an ion propagation axis 206D between input and output ends 218a, 218b, and a plurality of traveling wave electrodes sets 220a-220d that are adjacently situated between the RF electrodes 216a-216d also extend parallel to the ion propagation axis 206D. Each of the traveling wave sets 220a-220d includes respective traveling wave electrodes 222a-222d that receive respective time varying DC voltages or phase shifted AC voltages to form a traveling wave that urges or separates ions along the ion propagation axis 206D.

The electrode arrangement 200E includes a first set 224 of electrodes situated on the flexible substrate 202E1 that generally extend parallel to an ion propagation axis 206E and a second set 226 of electrodes situated on the flexible substrate 202E2 that extend convergently along the ion propagation axis 20EG. In some examples the flexible substrate 202E2 can be a separate substrate, and in other examples the flexible substrate 202E2 can be an extension of the flexible substrate 202E1. The flexible substrate 202E1 can form an electrode layout in an ion passageway 228 of a corresponding flexible ion conduit 230 along a flexible constant diameter section 232, and the shape of the flexible substrate 202E2 and the convergence associated with the electrodes of the second set 226 can form an electrode layout in the ion passageway 228 in a flexible tapered electrode section 234 of the flexible ion conduit 230.

As shown, the electrodes of the first set 224 can include a plurality of RF electrodes 236a-236f with adjacently alternating phases that direct ions away from the flexible substrate 202E1 and a plurality of traveling wave electrode sets 238a-238f including respective traveling wave electrodes 240a-240d that can urge or separate ions along the ion propagation axis 206E. The electrodes of the second set 226 generally include a related set of RF electrodes 236g-236k situated to form an extension of the respective RF electrodes 236a-236i. In some examples, to allow sufficient space between electrodes at the tapered end of the second set 226, fewer electrodes can be present at the tapered end. In further examples, an electrode reduction can occur along a tapered section. In additional embodiments, no electrode reduction is present in a tapered section. The second set 226 also includes a set of traveling wave electrode sets 238g-238k having respective traveling wave electrodes 240e-240h that can form an extension of the respective traveling wave electrode sets 238a-238c. In typical examples, time-varying DC voltages applied to the traveling wave electrode sets 238a-238f form a traveling wave along (and convergently along) the ion propagation axis 206E. It will be appreciated that various other electrode configurations can also be used to form tapered electrode arrangements in flexible ion conduits, such as the flexible ion conduit 230.

In the electrode arrangement 200F, a plurality of RF electrodes 242 including form an array of alternating RF phase both along and perpendicular to an ion propagation axis 206F. While equally spaced squares are shown, it will be appreciated that other dimensions, aspect ratios, shapes, spacings, and array configurations are possible, including different numbers of electrode columns. In the electrode arrangement 200G, a plurality of RF electrodes 244 form an array of alternating RF phase both along and perpendicular to the an ion propagation axis 206G, and a plurality of traveling wave electrode sets 246a-246c extending along the ion propagation axis 206G with respective traveling wave electrodes 248a-248e.

The electrode arrangement 200H includes a plurality of laterally extending RF electrodes 250a-250o arranged in a column along an ion propagation axis 206H. Adjacent ones of the RF electrodes 250a-250o have an opposite phase so that the RF electrodes 250a-250o can direct ions away from the flexible substrate 202H. In some examples, selected ones of the RF electrodes 250c, 250f, 250i, 250l, 250o can be configured as a traveling wave electrode set that receives a time varying DC voltage that urges or separates ions along the ion propagation axis 206H. The electrode arrangement 200I includes a plurality of RF electrode columns 252a-252c with respective RF electrodes 254a-254c and interposed traveling wave electrode sets 256a-256c. The RF electrode columns 252a-252c and traveling wave electrode sets 256a-256c can extend parallel to an ion propagation axis 206I. Adjacent electrodes 254a-254c in the respective RF electrode column 252a-252c have an alternating opposite phase at the applied modulation frequency. In some examples, the laterally adjacent electrodes 254a-254c in a selected row can have the same phase, and in other examples an opposite phase.

Figure 3:
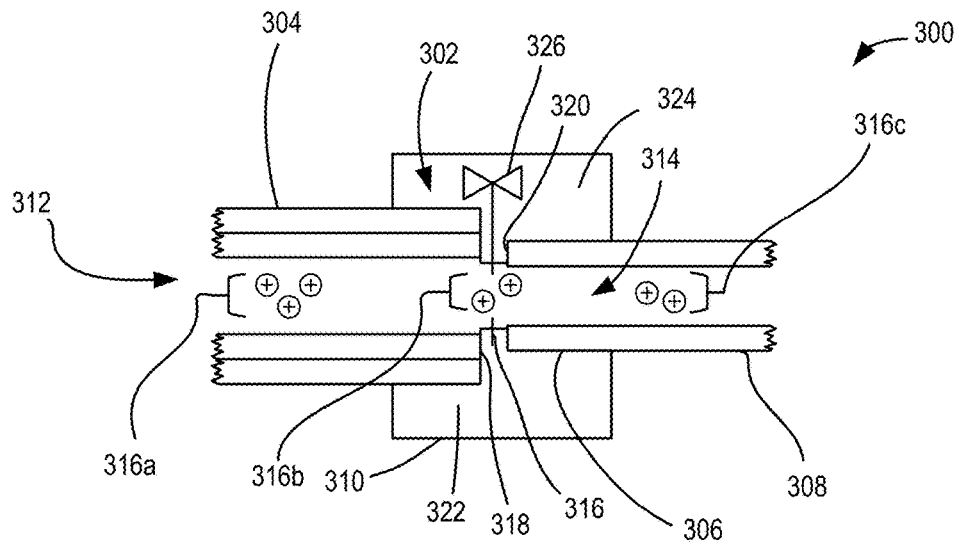
FIGS. 3-5 show side view cross-sections of examples of flexible ion conduit output couplings.

FIG. 3 is an ion transport coupling 300 of an output end 302 of a flexible ion conduit 304 to an ion inlet 306, such as a tube or nozzle, of an ion receiving device 308, such as a time-of-flight mass spectrometer, detectors, Faraday plates, electron multipliers, voltage amplifiers, pico-ammeters, etc. The ion transport coupling 300 includes a passageway coupler 310 adapted to receive and secure the output end 302 in relation to the ion inlet 306 so that an ion passageway 312 of flexible ion conduit 304 is in communication with an ion passageway 314 of the ion inlet 306, and ions 316a-316c can be directed into ion passageway 314 from the ion passageway 312. In representative embodiments, the ion passageway 314 defines a first lower pressure region of the ion receiving device 308, such as a first low pressure region of a mass spectrometer or other instrument. In some examples, the passageway coupler 310 can include a flanged member 316 that receives an endface 318 of the output end 302 and an endface 320 of the ion inlet 306, though in other examples the endfaces 318, 320 can also adjoin or be spaced apart by a selected or adjustable distance. In typical examples, the distance between the endfaces 318, 320 is small or negative (i.e., overlapping) to reduce ion loss in unguided passageway lengths. The passageway coupler 310 can include a receiving tube portions 322, 324 that can receive and secure the respective output end 302 and ion inlet 306. The receiving tube portions 322, 324 can include one or more threaded portions, colletts, set screws, clamps, adhesive, detents, interference diameters, etc., configured to hold the respective output end 302 and ion inlet 306. Various commercially available coupler fittings can be used, such as vacuum fittings, quick-connect/disconnects, hose clamps, etc.

In typical examples, the passageway coupler 310 is rigid or includes rigid portions, though the passageway coupler 310 can also include flexible members (including flexible flanged members, o-rings, receiving tubes, etc.) or be substantially flexible. To adapt or retrofit the flexible ion conduit 304 to the ion receiving device 308 that may be selected from a variety of available devices, dimensions of the ion inlet 306 and ion receiving device 308 can be measured, and based on the particular dimensions the passageway coupler 310 can be 3-D printed with thermoplastic or other suitable material, molded with a suitable mold, or adapted with shims, o-rings, or other material. The passageway coupler 310 can also include a passageway diameter control 326, such as a valve, iris, or nozzle, by way of example, that can extend from the flanged member 316 or axial position between the endfaces 318, 320 to vary a passageway diameter to control communication between the ion passageways 312, 314. As shown, the passageway coupler 310 is a single piece but it will be appreciated that two-piece or multi-piece couplers can be used, such as where a first piece includes the receiving tube portion 322 and the second piece includes the receiving tube portion 324. In some multi-piece examples, the different pieces can include respective portions of the flanged member 316 that can be used to secure the respective pieces at the flanged member 316.

Figure 4:
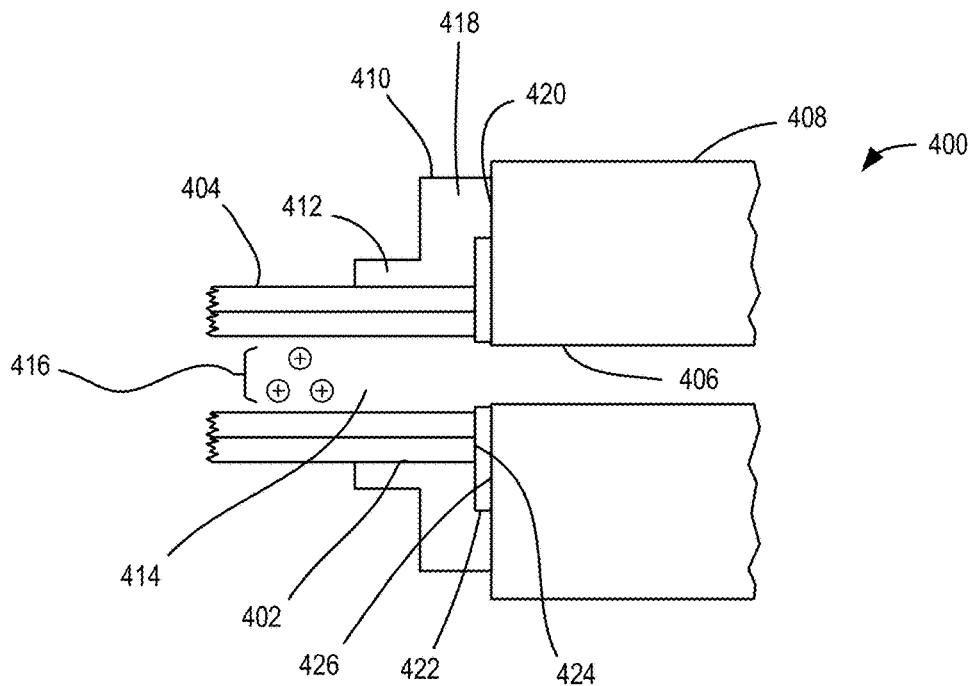

In FIG. 4, an ion transport coupling 400 couples an output end 402 of a flexible ion conduit 404 to an ion inlet 406 of an ion receiving device 408 with a passageway coupler 410. The passageway coupler 410 includes receiving tube portion 412 situated to receive and surround at least a portion of the output end 402. In representative examples, the receiving tube portion 412 holds the output end 402 so that an ion passageway 414 of the flexible ion conduit 404 that separates, stores, and/or propagates ions 416 can be secured in relation to the ion inlet 406. The passageway coupler 410 includes a flanged end 418 that can be secured to a receiving portion 420 of the ion receiving device 408, such as a mating surface, threads, protrusion, bore, slot, etc. In some examples, a compressive support member 422, such as an o-ring or washer, can be situated between an endface 424 of the flexible ion conduit 404 and an endface 426 of the ion receiving device 408 and can allow the output bend 402 and the receiving portion 420 to be brought closer together and snugly secured at the closer distance with the passageway coupler 410.

Figure 5:
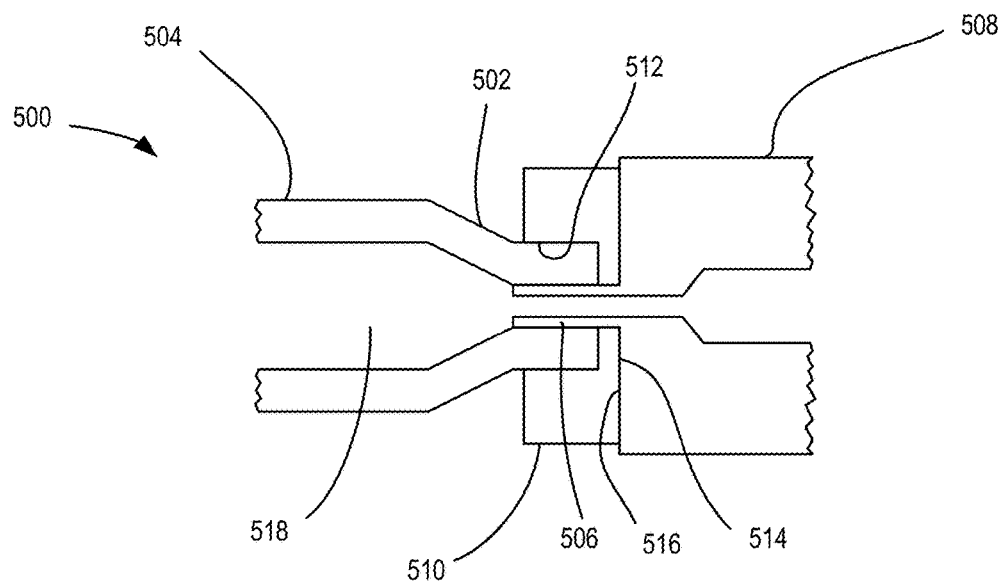

FIG. 5 is an example ion transport coupling 500 between an output end 502 of a flexible ion conduit 504 and an ion inlet tube 506 of an ion receiving device 508. A conduit coupler 510 includes a receiving portion 512 in which the output end 502 can be inserted. In some examples, the receiving portion 512 can be provided with a predetermined diameter that corresponds to insertion or interfering insertion of the output end 502. In further examples, the receiving portion 512 can form a clamp that secures the output end 502 to the ion inlet tube 506. A flanged surface 514 of the conduit coupler 510 can be secured to a receiving surface 516 of the mass spectrometer 508, in some embodiments. In some examples, a clamping or securing of the output end 502 provided by the receiving portion 512 can produce a tapering of the output end 502 and corresponding reduction in a diameter of an ion passageway 518 of the flexible ion conduit 504. In other examples, the output end 502 can be configured to have a tapered end before a securing of the output end 502 to the ion inlet tube 506. For some embodiments, the mass spectrometer 508 can include a pre-existing ion source (not shown) that is coupled to the ion inlet tube 506 with a coupler and/or coupling mechanism. The conduit coupler 510 or the output end 502 of the flexible ion conduit 504 can be configured with the same securing mechanism and dimensions as used with the ion source so that the ion source can be removed and replaced with the flexible ion conduit 504.

Figure 6:
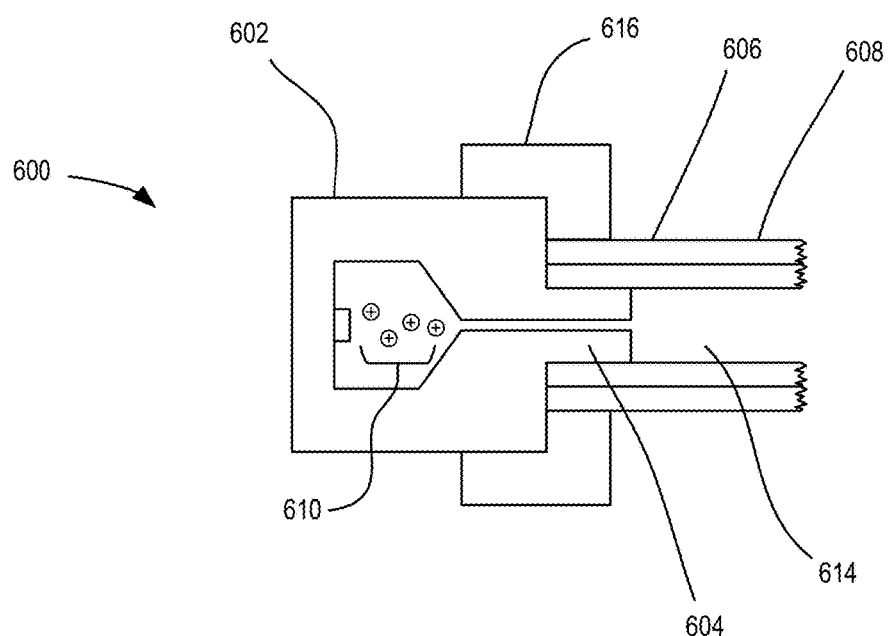
FIG. 6 shows a side view cross-section of an example flexible ion conduit input coupling.

An ion source coupling 600 in FIG. 6 couples an ion source 602, such as an electrospray ionization source (ESI) or a matrix-assisted laser desorption/ionization source (MALDI), situated to emit ions out of an output tube 604 or other orifice to an input end 606 of a flexible ion conduit 608. Ions 610 are generated by the ion source 602, typically at normal atmospheric pressure, and directed to propagate along an ion source passageway 612 and into an ion passageway 614 of the flexible ion conduit 608 that can be at a reduced pressure. The input end 606 can be secured to the output tube 604 in various ways to receive the ions 610. For example, a source coupler 616 can be secured to the flexible ion conduit 608 and the ion source 602 so that the ion source passageway 612 and the ion passageway 614 are in communication. In some examples, the source coupler 616 can clamp the input end 606 to the output tube 604. Some embodiments of the source coupler 616 can correspond to vacuum fittings or vacuum fitting components.

Figure 7:
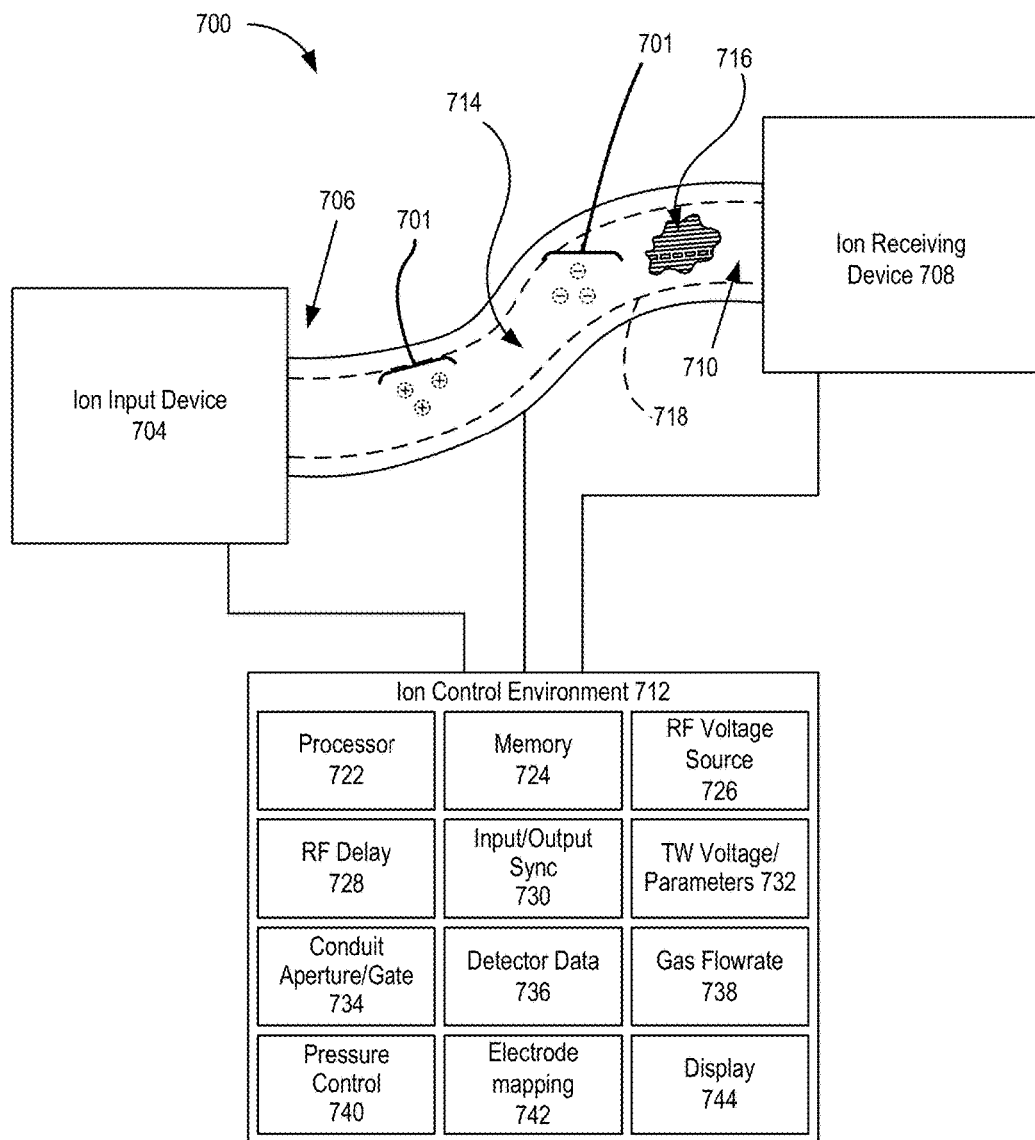
FIG. 7 shows a schematic of example ion control system.

FIG. 7 is a flexible ion conduit movement system 700 situated to move ions 701 in a flexible ion conduit 702 with high efficacy. In some examples, one or more ion input devices 704 can be coupled to an input end 706 of the flexible ion conduit 702, and one or more ion receiving devices 708 can be coupled to an output end 710 of the flexible ion conduit 702. In representative examples, the flexible ion conduit movement system 700 includes an ion control environment 712 that is coupled to the flexible ion conduit 702 to control the movement of the ions 701 in a flexible ion passageway 714 defined by the flexible ion conduit 702. In some examples, the ion control environment 712 also can be coupled to one or more of the input devices 704 and/or ion receiving devices 708, such as to control coupling of the ions 701 or fluids (e.g., gases) into or out of the input end 706 and into or out of the output end 710, or to detect movement or characteristics of the ions 701 (e.g., charge, polarity, mass, velocity, etc.).

In representative examples, the flexible ion conduit 702 includes an electrode arrangement 716 patterned on an inner surface 718 and facing the interior ion passageway 714 that is situated to allow for the application of voltages to provide electric fields that direct the ions 701 away from the inner surface 718 to reduce ion loss and allow ion transport, manipulation, separation, etc., of the ions 701 in the flexibly shaped ion passageway 714. In typical examples, the flexible ion conduit 702 comprises a tube or other shaped extended structure through which the ions 701 move in a gas from the input end 706 and the output end 710. The electrode arrangement 716 includes a plurality of RF electrodes adjacently receiving RF voltages of opposite polarity that creates a pseudo potential that prevents ions over a significant m/z range, such as in the range of 20 to 5000 m/z, or other m/z ranges, from closely approaching the inner surface 718. In some embodiments, the RF electrodes are arranged as electrode stripes extending longitudinally along a portion of or the entire length of the inner surface 718 of the flexible ion conduit 702. In further examples, the electrode arrangement 716 can further include a set of electrodes situated to receive dynamic voltages that are applied to produce electric traveling waves that move or assist with the movement of ions along the ion passageway 714, such as from the ion input device 704 to the ion receiving device 708. In additional examples, the electrode arrangement 716 can further include a set of electrodes that provides a voltage gradient along the length of the flexible ion conduit 702. To assist with the movement of the ions 701 in some embodiments, a gas can be flowed from the input end 706 to the output end 710, or from the output end 710 to the input end 706. The flowing gas can also be controlled to impede movement of the ions 701 and allow, e.g., for ion separation, ion storage, ion gating, or ion movement retardation. In some examples, a pressure variation produces a movement of the ions 701, such as by controllably supplying a gas to the ion passageway directly through a side of the inner surface 718 (at one or more positions) or based on pressure differences between a pressure of the ion input device 704 and a pressure of the ion receiving device 708. A range of pressure differences can be used, such as Δ0.01 torr, Δ1 torr, Δ10 torr, Δ100 torr etc., depend upon the length of the FLIP, the FLIP ion path cross section area, in ways well understood by those familiar with fluid dynamics in example tubes and similar gas flow conduits. The selected pressures can include ambient pressure or typical pressures for the first inlet stage of mass spectrometers (e.g. 0.1 to 10 torr). In some examples, a pressure range between the input end 706 and output end 710 can correspond to an ambient condition (760 torr) to a first stage of mass spectrometer at pressure of the order of a torr. In further examples, a pressure range can correspond to two distinct vacuum chambers at around the same pressure (e.g., 1 torr, 4 torr, 10 torr, etc.). In a particular example, an ion funnel can be operating at 4 torr and a SLIM device can be operating at a pressure 4.1 torr. It will be appreciated that various actual pressure quantities can be used these pressure numbers her are only a representation, and pressure differentials can vary with either inlet or outlet being higher or lower than the other while being at around the same order of pressure. In additional examples, a pressure range can correspond to a range of pressures where IMS is performed to pressures where mass analysis is performed. In other examples, a pressure range can correspond to any regime of pressure where ions are manipulated (e.g., ambient, ~1 torr pressure, or lower) to any pressure where detection is performed (e.g., ~1 torr, ~1 mtorr pressure or lower).

Examples of the flexible ion conduit movement system 700 can be used to move the ions 701 the ion input device 704 to the ion receiving device 706, such as between various instrument platforms, including from an ion mobility separation device to a mass spectrometer. In some examples, the ions 701 are moved from the input end 706 to the output end 710 without separation (e.g., with the RF electrodes), and in other examples, the ions 701 are continuously separated based on m/z and/or charge along at least a portion of the length of the flexible ion conduit 702, based on traveling wave parameters provided to the traveling wave electrodes. In some examples, the flexible ion conduit 702 of the flexible ion conduit movement system 700 can operate as a stand-alone ion mobility separator with an ion source, such as an ESI or MALDI source, corresponding to the ion input device 704. Traveling wave voltages can be used to advance and impede movement of selected ions.

The ion control environment 712 is typically coupled to the flexible ion conduit 702 and can be optionally coupled to one or more of the ion input devices 704 and the ion receiving devices 708, to control movement of the ions 701 in the ion passageway 714. The ion control environment 712 include one or more control devices, and can include at least a processor 722 and a memory 724. Control devices can include logic controllers, desktop or laptop computers, mobile devices, tablets, relays, manual controls, SCADA units, voltage sources and regulators, etc. The processor 722 can include one or more CPUs, GPUs, ASICs, PLCs, FPGAs, PLDs, CPLDs, etc., that can perform various data processing or I/O functions associated with the ion control environment 712. The memory 724 can be volatile or non-volatile (e.g., RAM, ROM, flash, hard drive, optical disk, etc.) and fixed or removable and is coupled to the processor 722. The memory 724 can provide storage capacity for one or more computer-readable media. One or more system buses 726 can provide a communication path between various environment components. The ion control system environment 712 can also be situated in a distributed form so that applications and tasks are performed by remote processing devices that are linked through a communications network. In a distributed computing environment, program modules and logic can be located in both local and remote memory storage devices.

The ion control environment 712 can include an RF voltage source 726 that provides the electric potential applied to the RF electrodes of the electrode arrangement 716. An RF phase control 728 can be used to vary an RF phase so that adjacent RF electrodes in the electrode arrangement 716 can be provided with an alternating RF voltage with a predetermined out-of-phase relationship (e.g., 180 degrees). An input/output synchronization 730 can be used to synchronize voltage characteristics between selected voltages of the electrode arrangement 716 and electrode voltages, ion timings, pulses, gates, space charge, or other controls of ion movement provided by the ion input device 704 feeding the ions 701 to the flexible ion conduit 702 and/or by the ion receiving device 708 that receives the ions 701. For example, some embodiments can use space charge to augment or replace traveling wave electrodes situated to produce ion movement. In space charge examples, FLIP electrodes can provide sufficient confinement away from the surface of the electrodes, and with excessive amounts of charge due to ions being moved to a specific region, space charge can redistribute the ions in specific ways (which may be exploited for any number of applications like chemical identification, ion activation, mass/mobility based segregation, etc.) without losses. Space charge can also be useful for pushing ions thru the FLIP. For example, the charge build up can result in the expansion of the ion cloud in the direction of least resistance (down the FLIP conduit). The ion control environment 712 can also include a traveling wave voltage source 732 (e.g., as part of the RF voltage source 726) configured to provide traveling wave voltages to the traveling wave electrodes of the electrode arrangement 716 according to different traveling wave parameters, such as DC voltage, wave speed, timing, AC phase shift. In typical examples, the traveling wave voltages provide movement along the ion passageway 714 of the ions 701 that are confined in the ion passageway 714 with the RF electrodes of the electrode arrangement 716.

One or more apertures or orifice valves of the flexible ion conduit 702 or of the ion input device 704 or ion receiving device 708 can be controlled with a conduit aperture/gate control 734. In some examples, the ion receiving device 708 can correspond to an ion detector and the ion control environment 712 can be configured to receive detector data 736 from the ion detector to determine the presence, amount, or other characteristics of detected ions. In some embodiments of the flexible ion conduit 702, one or more detectors (e.g., current detectors) can be placed in the ion passageway 714 to detect characteristics of the ions 701. The ion control environment 712 can include one or more controls for gas flowrate 738 and/or pressure 740 associated with one or more of the flexible ion conduit 702, ion input device 704, and ion receiving device 708. For example, the pressure control 740 can control a pressure of the flexible ion conduit 702 in relation to a pressure of a device to which the flexible ion conduit 702 is coupled, such as the ion input device 704 and/or ion receiving device 708 so as to provide an equal pressure or a controlled gradient and gas-flow. The gas flowrate 738 can assist with separation or movement of the ions 701 with a flow and flowrate along a common direction or along an opposite direction of the movement of the ions 701. In typical examples, the flexible ion conduit 702 includes a conductive trace coupled to the electrode arrangement 716, such as a separate flexible layer, so that the different voltages with respective characteristics (including DC, AC, time-varying, phase, amplitude) can be routed and applied to the different electrodes of the electrode arrangement 716 to produce corresponding ion movements, including voltages by the RF voltage source 726 and/or traveling wave voltage source 732. In some examples, multiple electrodes can be traced in parallel so as to receive a common voltage, such as multiple alternate RF electrodes at a selected phase or multiple adjacent traveling wave electrodes at a selected position along the ion passageway 714. In some examples, at least a portion of the electrodes of the electrode arrangement 716 can be separately provided selected voltages based on an electrode mapping 742. The electrode mapping 742 can be used to reconfigure voltage assignments for different electrodes of the electrode arrangement 716, e.g., by converting a longitudinal series of electrodes configured to receive a single RF potential to receive a traveling wave potential instead, providing a first set of two adjacent RF electrodes with a common phase and second set of two RF electrodes adjacent to the first set with a common phase opposite the first set, etc. The various controls of the ion control environment 712, including RF and traveling wave voltages, can be selected to produce ion movement and/or separation based on charge or m/z along the ion passageway 714. A display 742 can be situated to display ion characteristics, detected data, performance of the ion receiving device 708 and/or ion input device 704, or provide a user interface for various controls of the ion control environment 712 such as voltage selection, ion movement and/or separation characteristics, etc.

Figure 8:
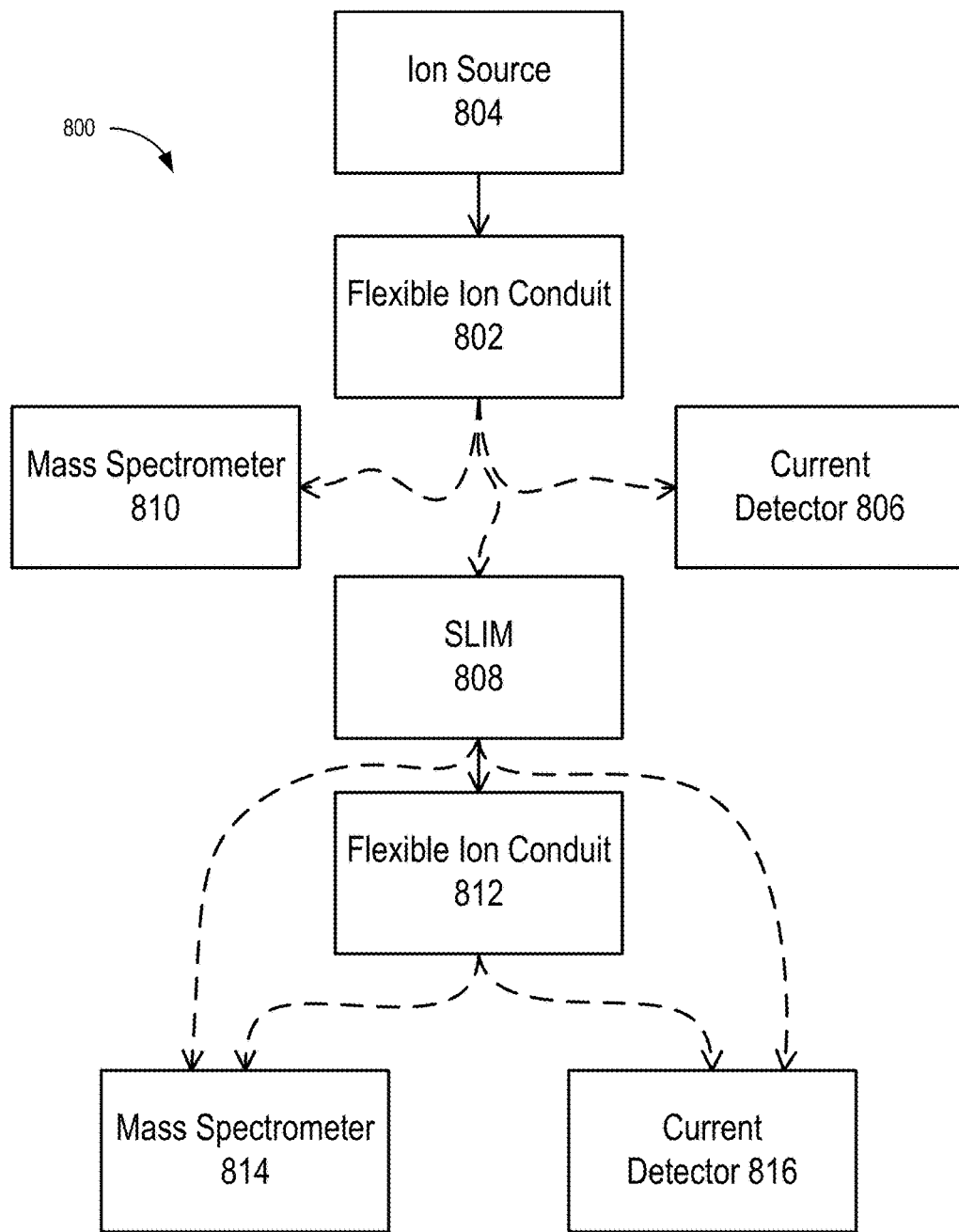
FIG. 8 shows examples of configurable flexible ion conduit systems.

FIG. 8 is a configurable ion manipulation system 800 that includes a flexible ion conduit 802 having a patterned electrode arrangement situated to move, separate, and/or manipulate ions in an internal flexible ion passageway. The flexible ion conduit 802 can be flexibly coupled to an ion source 804, such as an ESI or MALDI source, or from another suitable ion source, such as another flexible ion conduit or a location having material containing ions to be detected. Other suitable ion sources can include chemical ionization sources, atmospheric pressure, sub-ambient or ambient ionization sources, inductively coupled plasmas, photoionization devices and sources, gas chromatographs, etc. In some examples, the ion source 804 can include various instruments, such as ion mobility spectrometers, a structure for lossless ion manipulation (SLIM), liquid chromatograph, gas chromatograph, etc. In some examples, the flexible ion conduit 802 can be flexibly directed to a current detector 806 or other suitable detector, such as an electron multiplier, ion/charge detector, optical detector, Faraday plates, etc. In some examples, the flexible ion conduit 802 can be used effectively as an ion mobility analyzer. In some of such examples, the flexible ion conduit 802 can operate similar to a SLIM that losslessly separates and/or manipulates ions along the ion passageway. Examples of SLIM devices are disclosed in, e.g., U.S. Pat. No. 8,835,839, which is incorporated by reference herein in its entirety. Use of the flexible ion conduit 802 as a SLIM or to direct ions to the current detector 806 can allow for remote sampling of ions such that ions can be created or sampled remotely from a bulkier instrument, such as a mass spectrometer. Representative systems can also flexibly couple the flexible ion conduit 802 to a mass spectrometer 810 or other instrument, such as an ion mobility analyzer. Other suitable instruments can include ion mobility spectrometers. In further examples, the flexible ion conduit 802 is flexibly coupled to a SLIM device 808. In various embodiments, the output of the SLIM 808 can be coupled to another flexible ion conduit 812, mass spectrometer 814 (or other instrument), or current detector 816. Alternatively, the flexible ion conduit 812 can be coupled to the mass spectrometer 814 or current detector 816. The flexible ion conduits 802, 812 can be used to extend lengths and relative positions between different devices, allowing greater flexibility in positioning of instrumentation. The flexible ion conduits 802, 812 can also be adapted to various device inputs with different couplers or conduit dimensions and/or tapers or expanders, so as to allow for interchangeability between instrumentation devices or adapting different device inputs to different device outputs. Thus, it will be appreciated that in view of the above, a non-exhaustive list of possible system examples and arrangements that can be coupled with the flexible ion conduit can include an ion source and mass spectrometer, an ion source and ion mobility spectrometer, an ion mobility spectrometer and a mass spectrometer, an ion source and SLIM, a SLIM and mass spectrometer, an ion mobility spectrometer and a SLIM, a liquid or gas chromatograph and SLIM, a liquid or gas chromatograph and an ion mobility spectrometer, or a liquid or gas chromatograph and mass spectrometer.

Figure 9:
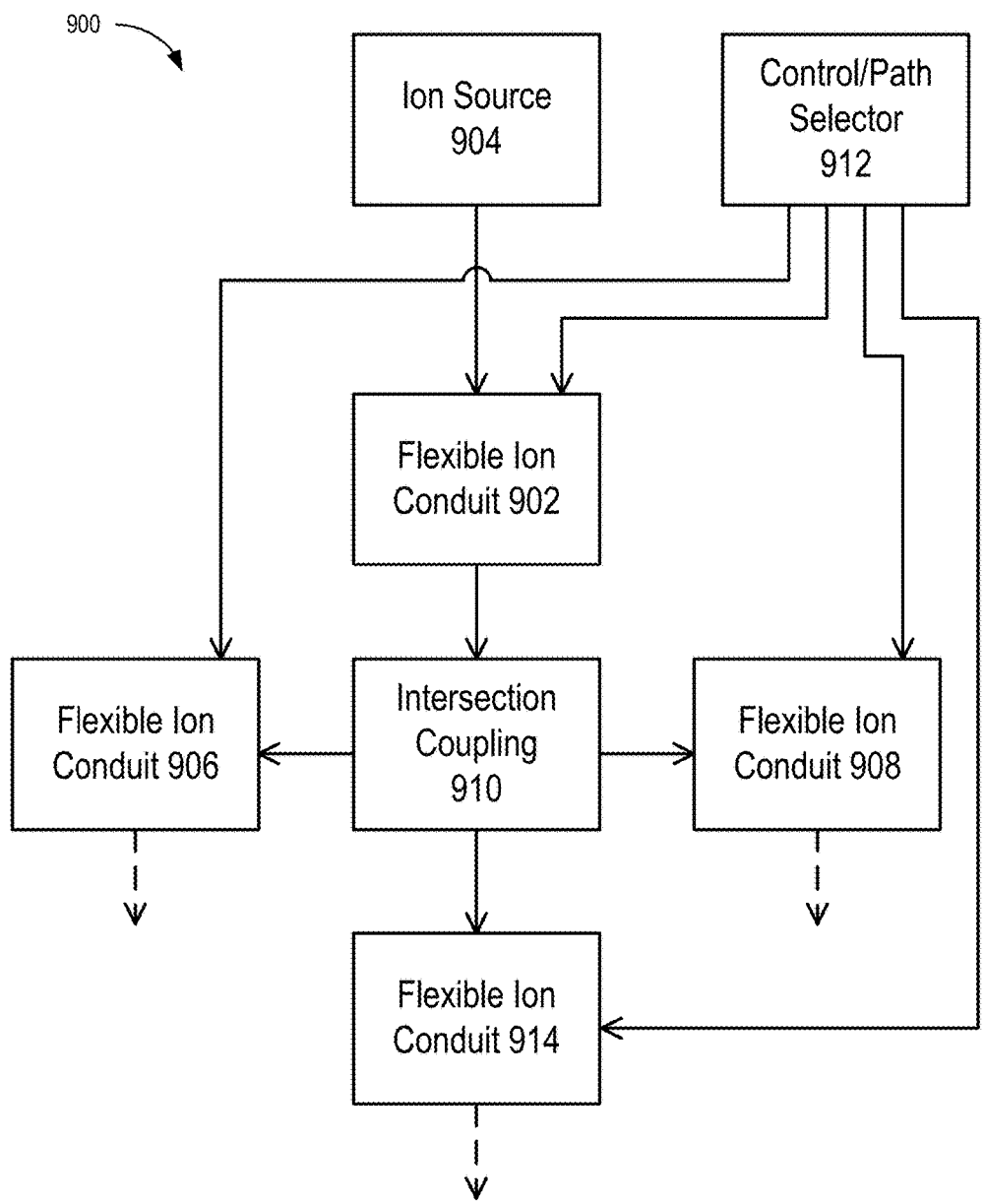
FIG. 9 shows examples of ion switches.

FIG. 9 is an ion switching system 900 that includes a flexible ion conduit 902 situated to receive ions from an ion source 904. The flexible ion conduit 902 is coupled to a first output flexible ion conduit 906 defining a first ion path, and a second output flexible ion conduit 908 defining a second ion path, with an intersection coupling 910. In some examples, the intersection coupling 910 can be a separate rigid or flexible component, such as a T-shaped, Y-shaped, or cross-shaped coupler that receives an output of the flexible ion conduit 902 and inputs of the first and second output flexible ion conduits 906, 908. In further examples, the intersection coupling 910 can be part of a single flexible conduit assembly so that the flexible ion conduit 902 and the first and second output flexible ion conduits 906, 908 are integrated into a single piece. A ion path selection control 912 can be coupled to one or more of the flexible ion conduit 902 and first and second output flexible ion conduits 906, 908 (or intersection coupling 910) so as to select or vary a movement path or characteristic of ions propagating in the flexible ion conduit 902. For example, traveling wave electrode voltages in one or more (including all) of the flexible ion conduits 902, 906, 908 can be coordinated with the ion path selection control 912 to direct ions propagating in the flexible ion conduit 902 into one or both of the first and second output flexible ion conduits 906, 908. Ions that are directed into different flexible ion conduits, such as the first and second output flexible ion conduits 906, 908, can define trapping volumes for storing ions. It will be appreciated that in some embodiments additional flexible ion conduits or rigid outputs can be coupled to the flexible ion conduit 902 at the intersection coupling 910. In some examples, the intersection coupling 910 can be cross-shaped and provide more than two output paths, e.g., by including a third flexible ion conduit 914. The flexible ion conduit 914 can also be coupled to the ion path selection control 912.

Figure 10:
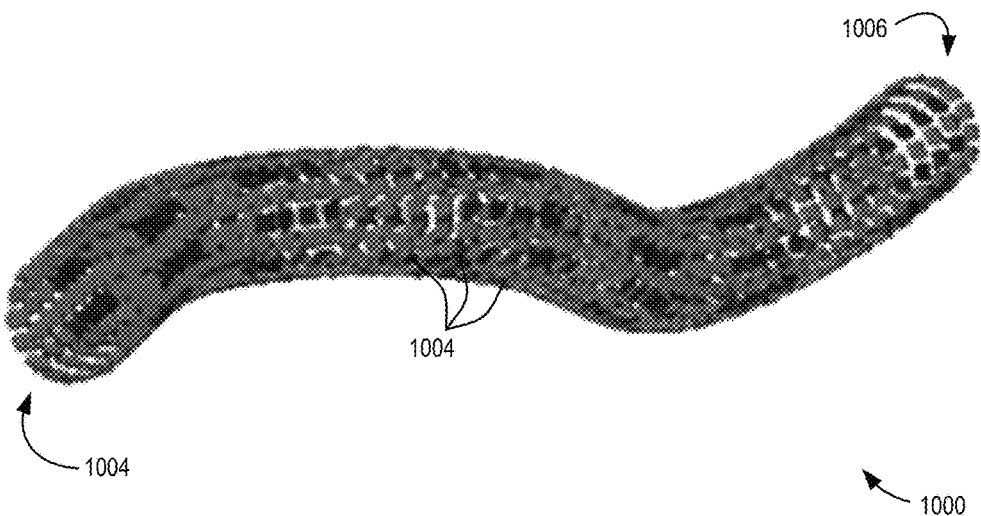
FIG. 10 shows a perspective view of an electrode arrangement of an example flexible ion conduit.
Figure 11:
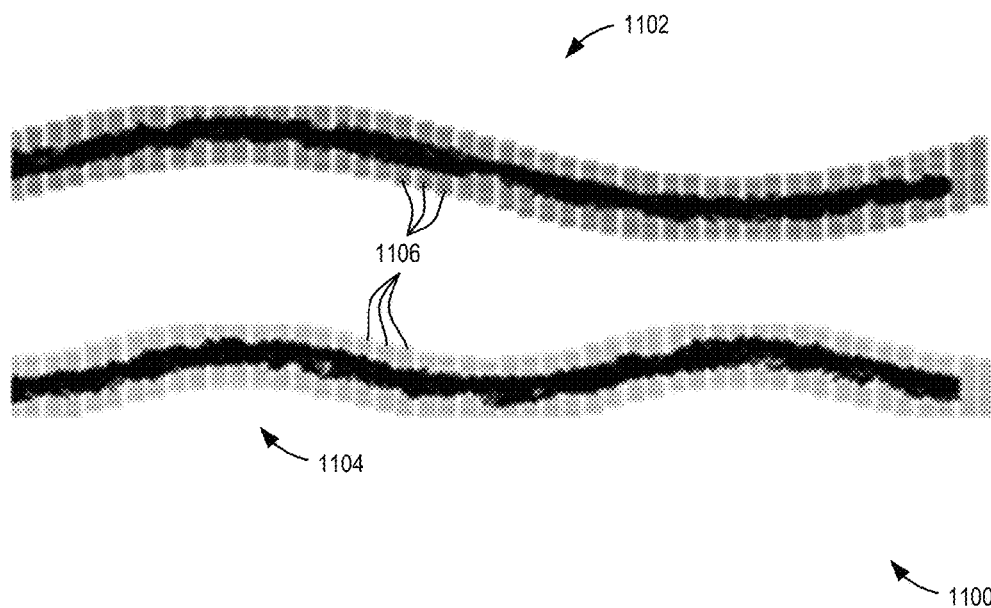
FIG. 11 shows side cross-sections of a flexible ion conduit in different bent configurations.
Figure 12:
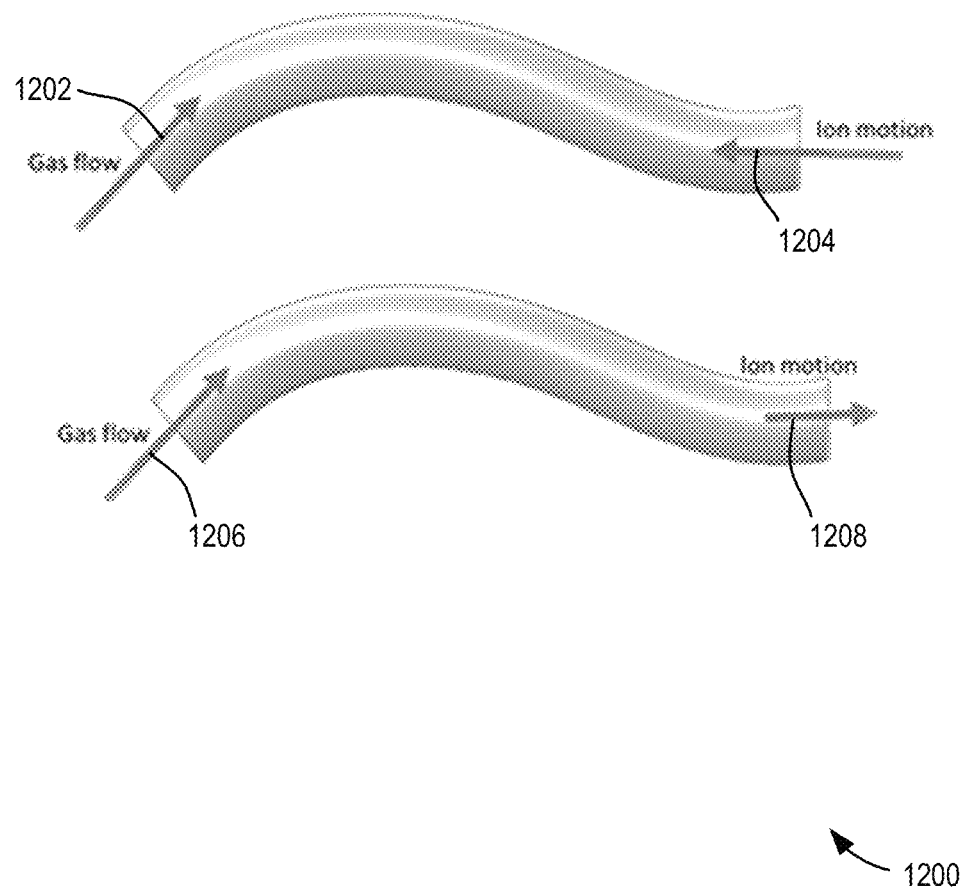
FIG. 12 shows examples of flexible ion conduits using gas flows.

FIG. 10 is a flexible ion conduit 1000 that includes a plurality of separate electrodes 1002 arranged circumferentially and longitudinally on an inner surface (not shown for clarity). The shape of the flexible ion conduit 1000 can be manipulating in various way, such as by bending, twisting, etc., and the electrodes 1002 keep ions in the flexible ion conduit 1000 so that the ions can be moved from an input end 1004 to an output end 1006, separated within the flexible ion conduit 1000, or stored within flexible ion conduit 1000. FIG. 11 is a flexible ion conduit 1100 shown in two different bent configurations 1102, 1104. The flexible ion conduit 1100 includes a plurality of ring-shaped RF electrodes and/or traveling wave electrodes 1106 that prevent ions 1108 from contacting the 1106 and that urge the ions 1108 along the flexible ion conduit 1100. FIG. 12 is a flexible ion conduit 1200 showing a gas flow 1202 in the same direction as ion movement 1204 and a gas flow 1206 in an opposite direction of ion movement 1208.

FIGS. 15A-15C show an example of a flexible ion conduit 1500 in a quadrupole-like configuration. The flexible ion conduit 1500 includes an electrode arrangement 1502 including traveling wave electrode sets 1504a-1504h that extend longitudinally along the flexible ion conduit 1500, and that receive time dependent traveling wave voltages along the length, e.g., as depicted with the shading variation in FIG. 15A. RF electrodes 1506 are situated between the traveling wave electrode sets 1504a-1504h and have lengths along the longitudinal direction of the flexible ion conduit 1500 that can be similar or different from the electrodes of the traveling wave electrode sets 1504a-1504h. As shown, the lengths of the RF electrodes 1506 are substantially shorter than the length of the flexible ion conduit that can be associated with the flexure ability of the flexible ion conduit 1500. In the quadrupole-like configuration, the RF electrodes 1506 that are situated between adjacent sets of the traveling wave electrode sets 1504a-150h, e.g., between traveling wave electrode sets 1504a, 1504b, receive a common in-phase RF voltage (+). The RF electrodes 1506 that are situated between neighboring adjacent sets of the traveling wave electrode sets 1504a-1504h, e.g., between traveling wave electrode sets 1504b, 1504c or 1504h, 1504a are receive a common in-phase RF voltage (−) that is 180 degrees out of phase from the RF voltage (+). Thus, RF voltage phases alternate radially around the circumference of the flexible ion conduit 1500. A simulated electro-potential heatmap 1508 is shown in FIG. 15C for the cross-section shown in FIG. 15B. As shown in FIG. 15A, the thickness of the electrodes 1506 and traveling wave electrodes of the traveling wave electrode sets 1504a-1504h are exaggerated. Typical electrode thicknesses include 0.01 cm, 0.1 cm, 0.5 cm, 1 cm, etc.

FIGS. 16A-16C depict an example of a flexible ion conduit 1600 providing an electrode arrangement 1602 with RF electrodes receiving alternating RF voltage phases in an axial and radial direction. The electrode arrangement 1602 includes a plurality of traveling wave electrode sets 1604a-1604h extending along the length of the flexible ion conduit 1600. A plurality of RF electrodes 1606 are situated between the traveling wave electrode sets 1604a-1604h and receive RF voltages with the RF electrodes 1606 that are adjacently longitudinal receiving an RF voltage with opposite phase, and with the RF electrodes 1606 that are radially adjacent (e.g., adjacent to an electrode of an adjacent traveling wave electrode set) also receiving an RF voltage with the opposite phase. For example, RF electrodes 1606 with a (+) designation are have a common phase and RF electrodes 1606 with a (−) designation have a common phase that is 180 degrees opposite of the (+). A simulated electro-potential heatmap 1608 is shown in FIG. 16C for the cross-section shown in FIG. 16B.

FIGS. 17A-17D show an example of a flexible ion conduit 1700 having an electrode arrangement 1702 that generally includes a plurality of traveling wave electrode sets 1704a-1704h and RF electrodes 1706. Adjacent ones of the RF electrodes 1706 in a common cross-section have a common RF voltage phase, such as shown in the different selected cross-sections in FIGS. 17B-17C. In typical examples, longitudinally adjacent ones of the RF electrodes 1706 have an opposite phase, such that adjacent cross-sections of flexible ion conduit 1700 have RF electrodes with an opposite voltage phase relationship. A simulated electro-potential heatmap 1708 is shown in FIG. 17D for the cross-section shown in FIG. 17B.

Figure 18:
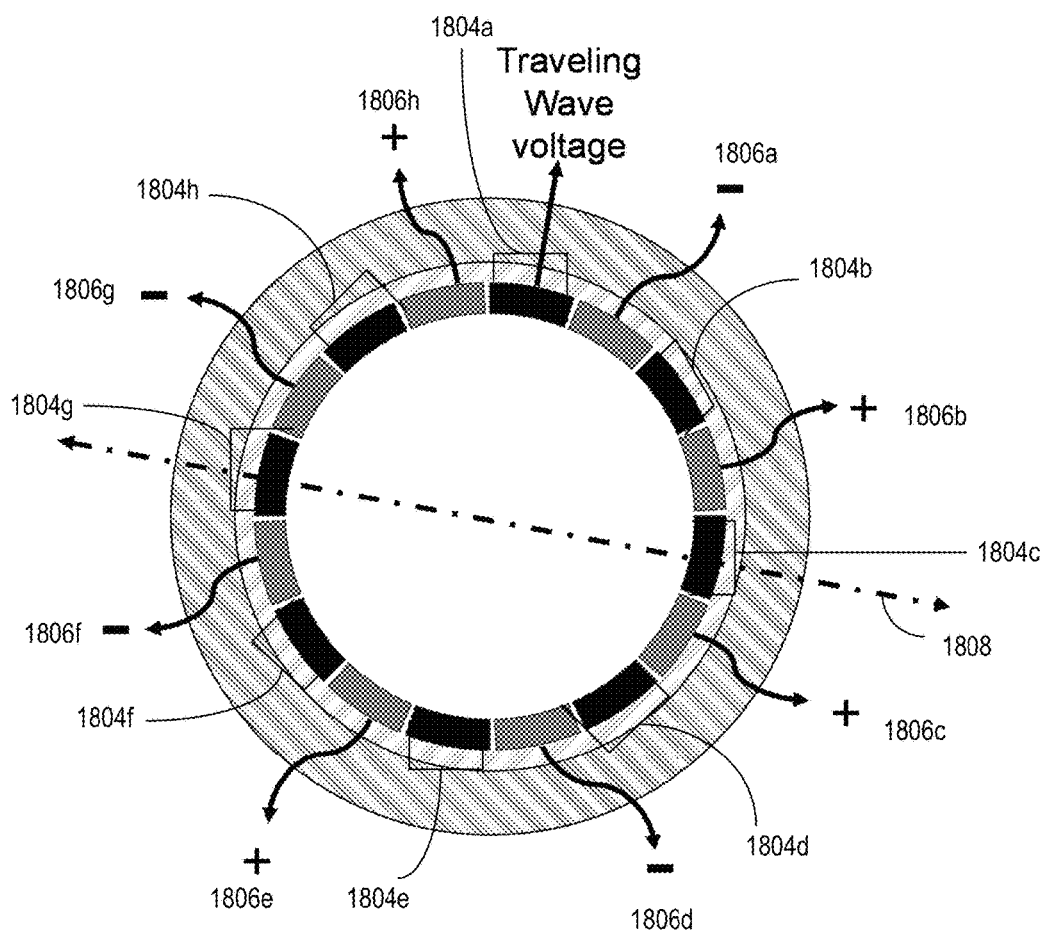
FIG. 18 shows an example of a flexible ion conduit in cross-section.

FIG. 18 shows a cross-section of an example flexible ion conduit 1800 that includes an electrode arrangement 1802 that can correspond to a flexibly circular structure for lossless ion manipulation. The electrode arrangement 1802 includes a plurality of traveling wave electrode sets 1804a-1804h and a plurality of RF electrodes 1806a-1806h. As shown, the electrode arrangement 1802 is symmetric about a symmetry axis 1808 that is generally perpendicular to a longitudinal axis 1810 that extends into the plane of FIG. 18. Thus, the RF electrode pairs 1806a, 1806d, and 1806f, 1806g have a common RF voltage phase. RF electrode pairs 1806b, 1806c, and 1806e, 1806h also have a common RF voltage phase that is opposite that of the RF electrodes 1806a, 1806d, 1806f, 1806g. The RF electrodes 1806a-1806h can extend longitudinally along an entire length of the flexible ion conduit 1800 or a plurality can extend in series along the length of the flexible ion conduit 1800, including with a common phase longitudinally or with alternating phase longitudinally. Some embodiments can also be circular and provided with an electrode symmetry axis to allow lossless ion manipulation. In typical examples, the electrode symmetry axis also corresponds to a cross-sectional geometric symmetry (e.g., rectangle, ellipse, etc.).

Figure 19A:
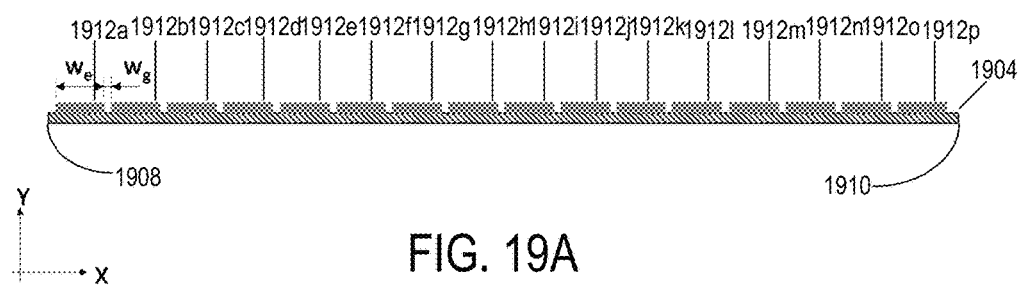
FIGS. 19A-19D show an un-rolled cross-section, rolled cross-section, and a side rolled cross-section, and side view, of an example flexible ion conduit
Figure 19B:
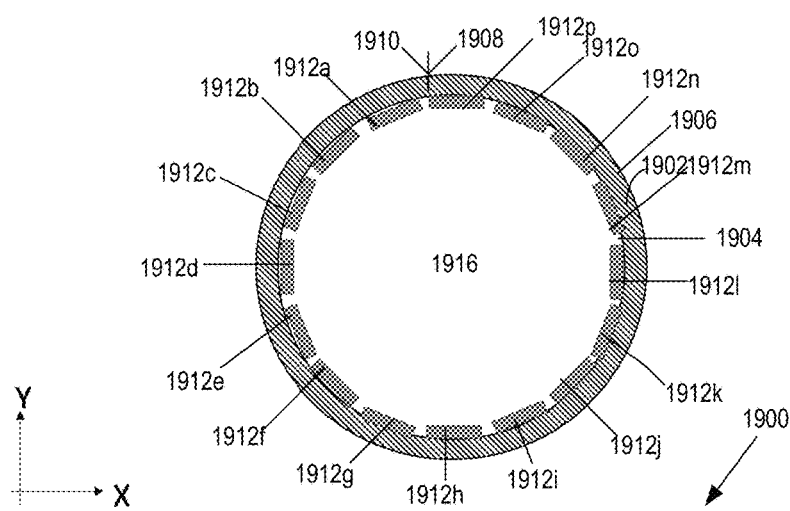
Figure 19C:
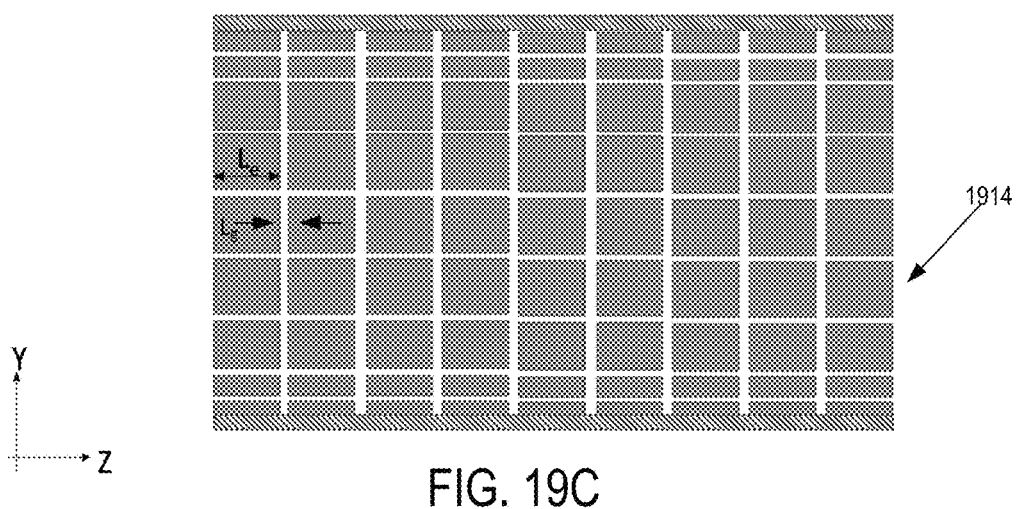
Figure 19D:
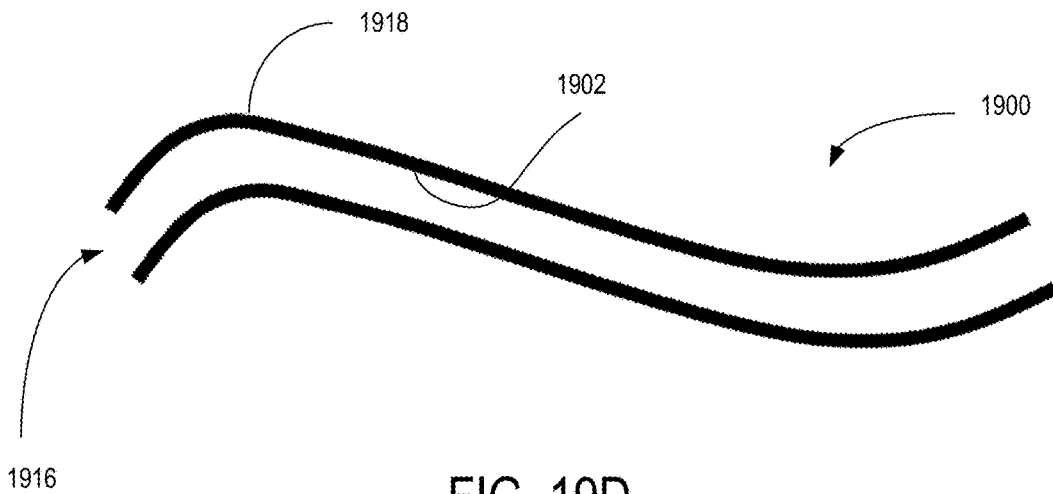

FIGS. 19A-19D depict a flexible ion conduit 1900 that includes a flexible electrode pattern substrate 1902 including opposite surfaces 1904, 1906 and side surfaces 1908, 1910. A plurality of electrodes 1912a-1912p are printed on the surface 1904, typically while the flexible electrode pattern substrate 1902 is secured in a predetermined position on a flat surface, to form an electrode arrangement 1914. In representative examples, the electrodes 1912a-1912p have a gap width ratio $w_g/w_e$ across a circumferential direction of the electrodes 1912a-1912p that is sufficiently small in relation to a selected diameter of an ion passageway 1916 (e.g., depicted in FIG. 19B) such that the flexible electrode pattern substrate 1902 will retain flexibility and be allowed to become rolled up at the selected diameter by articulating between adjacent electrodes. Suitable gap width ratios include 0.01, 0.05, 0.1, 0.2, etc. (though typically smaller than 1), and can be limited by printing resolution. In typical examples, the plurality of electrodes 1912a-1912p have a rigidity associated with the presence of the electrode material, such as a printed electrode material thickness and/or elastic modulus. Circumferential gap widths are selected such that articulation into a rolled state, and flexible movement of the flexible ion conduit 1900 with the rolled flexible electrode pattern substrate 1902, does not produce an electrode deflection large enough to cause an electric short between adjacent electrodes. Example gaps can include 100 μm, 50 μm, 30 μm, 12 μm, or smaller. Thus, the flexibility of the flexible ion conduit 1900 is assisted in the case that the individual electrodes 1912a-1912p are not flexible by maintaining the ratio of electrode and inter-electrode gap so as to enable post-fabrication flexibility for the electrode pattern substrate 1902. In some examples, the aspect ratio and/or thickness of the electrodes 1912a-1912p in cross-section can allow the electrodes 1912a-1912p to be flexible for selected diameters of the ion passageway 1916. In such cases, the gap width ratio $w_g/w_e$ is typically selected to be as small as possible. As shown, electrode cross-sections are rectangular, however other cross-sections are possible, including trapezoidal, mesa-shaped, rounded, etc., which can also reduce the likelihood of contact between adjacent electrodes in a rolled state. As shown in FIG. 19C, the electrodes 1912a-1912p have a selected length $L_e$ in the longitudinal direction of the ion passageway 1916 and are separated by gaps $L_g$ in the longitudinal direction that can be the same as the width gap $w_g$. With a suitable selected $L_e/L_g$ ratio, such as 0.01, 0.05, 0.1, 0.2, etc. (though typically smaller than 1), the flexible electrode pattern substrate 1902 will remain flexible in the longitudinal direction (i.e., Z direction) of the flexible ion conduit 1900. In some examples, the side surfaces 1908, 1910 can be brought together and secured as a seam. In other examples, an inside diameter of a sheath 1918 in contact with the surface 1906 can correspond to the rolled diameter of the surface 1906 such that no gap or a minimal gap is present between the side surfaces 1908, 1910.

Figure 20:
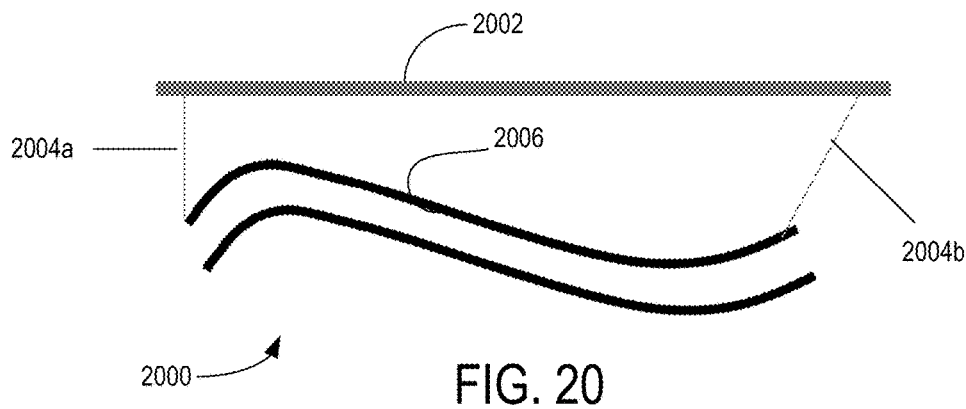
FIGS. 20-21 show side views of example flexible ion conduits coupled to electronic components.
Figure 21:
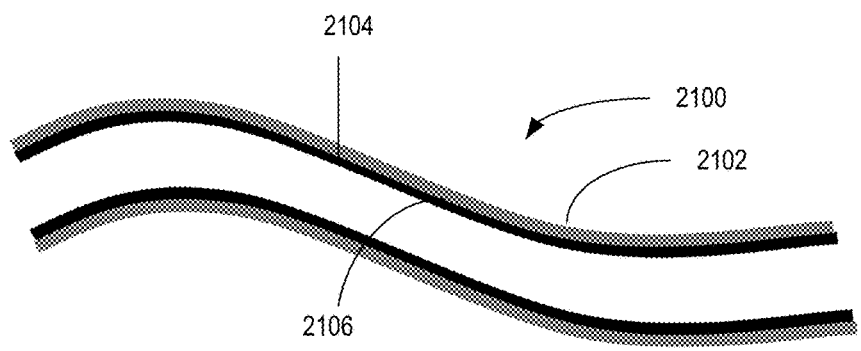

FIGS. 20-21 show examples of flexible ion conduits 2000, 2100. The flexible ion conduit 2000 is coupled to electronic components 2002, such as a motherboard and voltage source components. Harness wires 2004a, 2004b remotely couple the electronic components 2002 to an electrode arrangement 2006 of the flexible ion conduit 2000. The flexible ion conduit 2100 includes electronic components 2102 that are mounted to a flexible substrate or sheath 2104 of the flexible ion conduit 2100, and an electrode arrangement 2106 is coupled to the electronic components 2102.

In view of the many possible embodiments to which the principles of the disclosed technology may be applied, it should be recognized that the illustrated embodiments are only representative examples and should not be taken as limiting the scope of the disclosure. Alternatives specifically addressed in these sections are merely exemplary and do not constitute all possible alternatives to the embodiments described herein. For instance, various components of systems described herein may be combined in function and use. We therefore claim all that comes within the scope of the appended claims.

We claim:

1. An apparatus, comprising:
a flexible ion conduit extending between an input end situated to receive ions and an output end to deliver ions and defining an ion passageway, the flexible ion conduit including an inner conduit portion having an inner surface facing the interior ion passageway and having a plurality of RF electrodes situated to receive RF voltages wherein each RF voltage is out of phase with respect to the RF voltage applied to a nearest RF electrode of the RF electrodes to direct the received ions away from the inner surface of the ion passageway.

2. The apparatus of claim 1, wherein at least four of the RF electrodes extend along the inner surface for an entire length of the flexible ion conduit between the input end and the output end.

3. The apparatus of claim 1, wherein at least four of the RF electrodes extend along the inner surface for at least a portion of the length of the flexible ion conduit.

4. The apparatus of claim 3, wherein the plurality of RF electrodes is an even numbered quantity.

5. The apparatus of claim 4, wherein the portion is at least 80% of the length.

6. The apparatus of claim 1, wherein the inner conduit portion is cylindrical or deviates from a cylindrical by being elliptically cylindrical for some or all of a length of the flexible ion conduit.

7. The apparatus of claim 1, wherein the inner conduit portion includes a plurality of electrodes positioned between the RF electrodes and that is situated to receive AC or DC voltages and that forms an electrode set that extends along the inner surface for at least a portion of the length of the flexible ion conduit.

8. The apparatus of claim 1, wherein the inner conduit portion includes a plurality of traveling wave electrodes positioned between the RF electrodes and forming a set that extends along the inner surface for at least a portion of the length of the flexible ion conduit and that is situated to receive traveling wave voltages to form a traveling wave.

9. The apparatus of claim 8, wherein the traveling wave voltages correspond to time-varying DC voltages or phase shifted AC voltages.

10. The apparatus of claim 8, wherein the set of traveling wave electrodes and the traveling wave voltages are configured to direct the received ions from the input end to the output end.

11. The apparatus of claim 8, wherein the set of traveling wave electrodes and the traveling wave voltages are configured to receive and transmit ions of both positive and negative polarity simultaneously.

12. The apparatus of claim 8, wherein the set of traveling wave electrodes and the traveling wave voltages are configured to simultaneously receive, transmit, and separate ions of both positive and negative polarity based on their ion mobilities.

13. The apparatus of claim 8, wherein the set of traveling wave electrodes and the traveling wave voltages are configured to separate ions in the ion passageway based on ion mobility, m/z, and/or ion charge.

14. An apparatus, comprising:
a flexible ion conduit according to claim 8; and
a controller coupled to the flexible ion conduit and configured to control the traveling wave voltages applied to the set of traveling wave electrodes.

15. The apparatus of claim 1, wherein the RF electrodes are laterally separated from each other by non-conductive gaps of 30 μm or smaller but larger than a gap that causes an electrical breakdown between the RF electrodes.

16. The apparatus of claim 1, wherein the flexible ion conduit is situated to move ions along the ion passageway between the input end and the output end over a range of pressures based on a conduit length, cross-section, and gas flow.

17. The apparatus of claim 1, wherein the output end is configured to couple to a low pressure ion inlet for the low pressure ion inlet to receive the ions from the ion passageway.

18. The apparatus of claim 17, wherein the low pressure ion inlet is a mass analysis region of a mass spectrometer or an ion introduction component of the mass spectrometer ion inlet that is configured to deliver ions to the mass spectrometer.

19. The apparatus of claim 17, wherein the low pressure ion inlet is a structure for lossless ion manipulation (SLIM) ion inlet.

20. The apparatus of claim 1, further comprising a detector coupled to output end to detect one or more characteristics of the ions.

21. The apparatus of claim 1, wherein the flexible ion conduit comprises a bendable sheath surrounding the inner conduit portion and that supports the inner conduit portion and a pressure differential between an external pressure outside of the flexible ion conduit and an internal pressure in the ion passageway interior.

22. The apparatus of claim 21, wherein the external pressure is an ambient pressure.

23. The apparatus of claim 1, wherein the RF electrodes are configured to losslessly direct the ions into the ion passageway away from the inner surface across a predetermined range of bend radii of the flexible ion conduit.

24. The apparatus of claim 1, wherein the inner conduit portion contains arrays of electrodes patterned on a flexible printed circuit substrate.

25. The apparatus of claim 1, wherein the output end is tapered.

26. The apparatus of claim 1, further comprising an intersection coupling coupled to the output end and including a plurality of output ion paths for ions transported along the ion passageway.

27. The apparatus of claim 26, wherein the intersection coupling is a T-shaped, Y-shaped, or cross-shaped intersection coupling.

28. A method, comprising:
printing an electrode pattern of RF electrodes on a flexible printed circuit board to form the inner conduit surface of claim 1; and
securing the inner conduit surface in relation to a flexible sheath to form the flexible ion conduit.

29. A method, comprising:
exposing an ion inlet of an ion receiving device; and
coupling the flexible ion conduit of claim 1 to the ion inlet to provide an ion source for the ion receiving device.

30. The method of claim 29, wherein the ion inlet is a low pressure inlet of the ion receiving device.

31. The method of claim 29, wherein the exposing comprises removing an existing ion source mechanism coupled to the ion receiving device.

32. The method of claim 29, further comprising adapting an input aperture of the low pressure inlet to an output aperture of the flexible ion conduit.

33. The method of claim 29, wherein the ion receiving device is at least one of a mass spectrometer, ion mobility analyzer, structure for lossless ion manipulation (SLIM), liquid or gas chromatograph, and ion mobility spectrometer.

34. The method of claim 29, further comprising:
coupling the input end of the flexible ion conduit to an output of a structure for lossless ion manipulation;
wherein the ion receiving device is a mass spectrometer.

35. The method of claim 29, wherein the ion receiving device is an intersection coupling providing a plurality of selectable ion paths.

36. A method, comprising moving or separating the ions along the ion passageway of the flexible ion conduit of claim 1.

37. An apparatus, comprising:
a flexible ion conduit according to claim 1; and
a controller coupled to the flexible ion conduit and configured to control the RF voltages applied to the RF electrodes.

\* \* \* \* \*